United States Patent
Burns et al.

(10) Patent No.: US 7,737,143 B2
(45) Date of Patent: *Jun. 15, 2010

(54) SUBSTITUTED PYRAZINES AS KINASE INHIBITORS

(75) Inventors: Christopher John Burns, Caulfield Nth. (AU); Andrew Frederick Wilks, South Yarra (AU); Xianyong Bu, Viewbank (AU)

(73) Assignee: YM Biosciences Australia Pty Ltd, Melbourne (AU)

( * ) Notice: Subject to any disclaimer, the term of this patent is extended or adjusted under 35 U.S.C. 154(b) by 610 days.

This patent is subject to a terminal disclaimer.

(21) Appl. No.: 10/581,412

(22) PCT Filed: Dec. 3, 2004

(86) PCT No.: PCT/AU2004/001690

§ 371 (c)(1),
(2), (4) Date: Jun. 1, 2006

(87) PCT Pub. No.: WO2005/054230

PCT Pub. Date: Jun. 16, 2005

(65) Prior Publication Data

US 2007/0099935 A1     May 3, 2007

(30) Foreign Application Priority Data

Dec. 3, 2003 (AU) ............... 2003906686
Apr. 20, 2004 (AU) ............... 2004902060

(51) Int. Cl.
C07D 401/02 (2006.01)
C07D 241/20 (2006.01)
C07D 295/04 (2006.01)
A61K 31/497 (2006.01)
A61K 31/5355 (2006.01)
A61P 29/00 (2006.01)
A61P 25/28 (2006.01)
A61P 9/00 (2006.01)

(52) U.S. Cl. ............ 514/236.5; 544/120; 544/357; 544/405; 514/252.11; 514/255.05

(58) Field of Classification Search ........... 514/234.5, 514/254.06, 255.05, 236.5, 252.11; 544/139, 544/140, 370, 371, 405, 120, 357
See application file for complete search history.

(56) References Cited

U.S. PATENT DOCUMENTS 6,498,165 B1   12/2002   Armstrong et al.

FOREIGN PATENT DOCUMENTS

| WO | WO-00/62778 | 10/2000 |
| WO | WO-03/099811 | 12/2003 |

OTHER PUBLICATIONS

Vippagunta et al, "Crystalline Solids" Advanced Drug Delivery Reviews, vol. 48, pp. 3-26 (2001).*
Gavezzotti, "Are Crystal Structures Predictable?" Accounts of Chemical Research, vol. 27, pp. 309-314 (1994).*
Duhé et al, "Negative Regulation of Janus Kinases" Cell Biochemistry and Biophysics, vol. 34(1), pp. 17-59 (2001).*
Al-Dabbagh and Smith, "Species differences in oxidative drug metabolism: some basic considerations." Archives of toxicology. Supplement. Archiv fur Toxikologie. supplement, vol. 7, pp. 219-231 (1984).*
Hans Bundgaard, Design of Prodrugs, p. 1. © 1985 Elsevier Science Publishers.*
Richard B. Silverman, The Organic Chemistry of Drug Design and Drug Action, pp. 352-400. © 1992 Academic Press, Inc.*
International Search Report for PCT/AU2004/001690, mailed on Jan. 20, 2005, 2 pages.
Kozma et al., EMBO J. (1988) 7:147-154.
Sadowski et al., Mol. Cell. Biol. (1986) 6:4396-4408.
Spiotto and Chung, Prostate (2000) 42:88-98.
Wilks and Kurban, Oncogene (1988) 3:289-294.
Wilks et al., Mol. Cell. Biol. (1991) 11:2057-2065.

* cited by examiner

*Primary Examiner*—Susanna Moore
(74) *Attorney, Agent, or Firm*—Morrison & Foerster LLP

(57) ABSTRACT

A compound of general formula (I) or pharmaceutically acceptable prodrugs, salts, hydrates, solvates, crystal forms or diastereomers thereof is described. A method of treating kinase-associated disease states using the compound of formula (I) is also described.

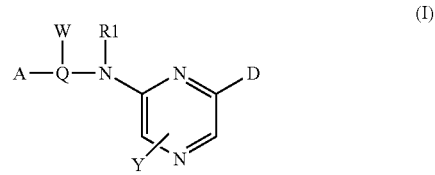

12 Claims, No Drawings

SUBSTITUTED PYRAZINES AS KINASE INHIBITORS

CROSS-REFERENCE TO RELATED APPLICATIONS

This application is the national stage of PCT application PCT/AU2004/001690 having an international filing date of 3 Dec. 2004, and claims the benefit of AU application 2003906686 filed 3 Dec. 2003, and AU application no. 2004902060 filed 20 Apr. 2004. The contents of these documents are incorporated herein by reference.

FIELD OF THE INVENTION

The present invention relates to the field of inhibitors of protein tyrosine kinases.

BACKGROUND OF THE INVENTION

Protein kinases are a family of enzymes that catalyse the phosphorylation of specific residues in proteins. In general protein kinases fall into several groups; those which preferentially phosphorylate serine and/or threonine residues, those which preferentially phosphorylate tyrosine residues and those which phosphorylate both tyrosine and Ser/Thr residues. Protein kinase are therefore key elements in signal transduction pathways responsible for transducing extracellular signals, including the action of cytokines on their receptors, to the nuclei, triggering various biological events. The many roles of protein kinases in normal cell physiology include cell cycle control and cell growth, differentiation, apoptosis, cell mobility and mitogenesis.

Protein kinases include, for example, but are not limited to, members of the Protein Tyrosine Kinase family (PTKs), which in turn can be divided into the cytoplasmic PTKs and the receptor PTKs (RTKs). The cytoplasmic PTKs include the SRC family, (including: BLK; FGR; FYN; HCK; LCK; LYN; SRC; YES and YRK); the BRK Family (including: BRK; FRK; SAD; and SRM); the CSK family (including: CSK and CTK); the BTK family, (including BTK; ITK; TEC; MKK2 and TXK), the Janus kinase family, (including: JAK1, JAK2, JAK3 and Tyk2), the FAK family (including, FAK and PYK2); the Fes family (including FES and FER), the ZAP70 family (including ZAP70 and SYK); the ACK family (including ACK1 and ACK2); and the Abl family (including ABL and ARG). The RTK family includes the EGF-Receptor family (including, EGFR, HER2, HER3 and HER4); the Insulin Receptor family (including INS-R and IGF1-R); the PDGF-Receptor family (including PDGFRα, PDGFRβ, CSF1R, KIT, FLK2); the VEGF-Receptor family (including; FLT1, FLK1 and FLT4); the FGF-Receptor family (including FGFR1, FGFR2, FGFR3 and FGFR4); the CCK4 family (including CCK4); the MET family (including MET and RON); the TRK family (including TRKA, TRKB, and TRKC); the AXL family (including AXL, MER, and SKY); the TIE/TEK family (including TIE and TIE2/TEK); the EPH family (including EPHA1, EPHA2, EPHA3, EPHA4, EPHA5, EPHA6, EPHA7, EPHA8, EPHB1, EPHB2, EPHB3, EPHB4, EPHB5, EPHB6); the RYK family (including RYK); the MCK family (including MCK and TYRO10); the ROS family (including ROS); the RET family (including RET); the LTK family (including LTK and ALK); the ROR family (including ROR1 and ROR2); The Musk family (including Musk); the LMR family including LMR1, LMR2 and LMR3); and the SuRTK106 family (including SuRTK106).

Similarly, the serine/threonine specific kinases comprise a number of distinct sub-families, including; the extracellular signal regulated kinases, (p42/ERK2 and p44/ERK1); c-Jun NH2-terminal kinase (JNK); cAMP-responsive element-binding protein kinases (CREBK); cAMP-dependent kinase (CAPK); mitogen-activated protein kinase-activated protein kinase (MAPK and its relatives); stress-activated protein kinase p38/SAPK2; mitogen- and stress-activated kinase (MSK); protein kinases, PKA, PKB and PKC inter alia.

Additionally, the genomes of a number of pathogenic organisms possess genes encoding protein kinases. For example, the malarial parasite *Plasmodium falciparum* and viruses such as HPV and Hepatitis viruses appear to bear kinase related genes.

Inappropriately high protein kinase activity has been implicated in many diseases resulting from abnormal cellular function. This might arise either directly or indirectly, for example by failure of the proper control mechanisms for the kinase, related for example to mutation, over-expression or inappropriate activation of the enzyme; or by over- or under-production of cytokines or growth factors also participating in the transduction of signals upstream or downstream of the kinase. In all of these instances, selective inhibition of the action of the kinase might be expected to have a beneficial effect. Diseases where aberrant kinase activity has been implicated include: diabetes; restenosis; atherosclerosis; fibrosis of the liver and kidney; ocular diseases; myelo- and lymphoproliferative disorders; cancer such as prostate cancer, colon cancer, breast cancer, head and neck cancer, leukemia and lymphoma; and, auto-immune diseases such as Atopic Dermatitis, Asthma, rheumatoid arthritis, Crohn's disease, psoriasis, Crouzon syndrome, achondroplasia, and thanatophoric dysplasia.

The JAK family of protein tyrosine kinases (PTKs) play a central role in the cytokine dependent regulation of the proliferation and end function of several important cell types of the immune system.

A direct comparison of the four currently known mammalian JAK family members reveals the presence of seven highly conserved domains (Harper et al, 1992). In seeking a nomenclature for the highly conserved domains characteristic of this family of PTKs, the classification used was guided by the approach of Pawson and co-workers (Sadowski et al, 1986) in their treatment of the SRC homology (SH) domains. The domains have been enumerated accordingly with most C-terminal homology domain designated JAK Homology domain 1 (JH1). The next domain N-terminal to JH1 is the kinase-related domain, designated here as the JH2 domain. Each domain is then enumerated up to the JH7 located at the N-terminus. The high degree of conservation of these JAK homology (JH) domains suggests that they are each likely to play an important role in the cellular processes in which these proteins operate. However, the boundaries of the JAK homology domains are arbitrary, and may or may not define functional domains. Nonetheless, their delineation is a useful device to aid the consideration of the overall structural similarity of this class of proteins.

The feature most characteristic of the JAK family of PTKs is the possession of two kinase-related domains (JH1 and JH2) (Wilks et al, 1991). The putative PTK domain of JAK1 (JH1) contains highly conserved motifs typical of PTK domains, including the presence of a tyrosine residue at position 1022 located 11 residues C-terminal to sub-domain VII that is considered diagnostic of membership of the tyrosine-specific class of protein kinases. Alignment of the human JAK1 PTK domain (255 amino acids), with other members of the PTK class of proteins revealed homology with other functional PTKs (for example, 28% identity with c-fes (Wilks and Kurban, 1988) and 37% homology to TRK (Kozma et al, 1988). The JH1 domains of each of the JAK family members possess an interesting idiosyncrasy within the highly conserved sub-domain VIII motif (residues 1015 to 1027 in JAK2) that is believed to lie close to the active site, and define substrate specificity. The phenylalanine and tyrosine residues flanking the conserved tryptophan in this motif are unique to the JAK family of PTKs. Aside from this element, the JH1 domains of each of the members of the JAK family are typical PTK domains.

The central role played by the JAK family of protein tyrosine kinases in the cytokine dependent regulation of the proliferation and end function of several important cell types means that agents which inhibit JAK are useful in the prevention and chemotherapy of disease states dependent on these enzymes. Potent and specific inhibitors of each of the currently known four JAK family members will provide a means of inhibiting the action of those cytokines that drive immune pathologies, such as asthma (e.g. IL-13; JAK1, JAK2), and leukemia/lymphoma (e.g. IL-2: JAK1 and JAK3).

Furthermore, certain types of cancer such as prostate cancer develop autocrine production of certain cytokines as a selectable mechanism of developing growth and/or metastatic potential. An example of this is cancer of the prostate, where IL-6 is produced by and stimulates the growth of prostate cancer cell lines such as TSU and TC3 (Spiotto M T, and Chung T D, 2000). Interestingly, levels of IL-6 are elevated in sera of patients with metastatic prostate cancer.

A great deal of literature covers the area of cytokine signalling. The present inventors have focussed on the JAK/STAT pathway that is involved in the direct connection of cytokine receptor to target genes (such as cell cycle regulators (e.g. p21) and anti-apoptosis genes (such as Bcl-$X_L$)).

The JAK/STAT Pathway

The delineation of a particularly elegant signal transduction pathway downstream of the non-protein tyrosine kinase cytokine receptors has recently been achieved. In this pathway the key components are: (i) A cytokine receptor chain (or chains) such as the Interleukin-4 receptor or the Interferon γ receptor; (ii) a member (or members) of the JAK family of PTKs; (iii) a member(s) of the STAT family of transcription factors, and (iv) a sequence specific DNA element to which the activated STAT will bind.

A review of the JAK/STAT literature offers strong support to the notion that this pathway is important for the recruitment and marshalling of the host immune response to environmental insults, such as viral and bacterial infection. This is well exemplified in Table 1 and Table 2. Information accumulated from gene knock-out experiments have underlined the importance of members of the JAK family to the intracellular signalling triggered by a number of important immune regulatory cytokines. The therapeutic possibilities stemming from inhibiting (or enhancing) the JAK/STAT pathway are thus largely in the sphere of immune modulation, and as such are likely to be promising drugs for the treatment of a range of pathologies in this area. In addition to the diseases listed in Tables 1 and 2, inhibitors of JAKs could be used as immunosuppresive agents for organ transplants and autoimmune diseases such as lupus, multiple sclerosis, rheumatoid arthritis, Type I diabetes, autoimmune thyroid disorders, Alzheimer's disease and other autoimmune diseases. Additionally, treatment of cancers such as prostate cancer by JAK inhibitors is indicated.

TABLE 1

| Disease Type | Cell Types Involved | Characteristics |
|---|---|---|
| Atopy | | |
| Allergic Asthma | Mast Cells | T-cell activation of |
| Atopic Dermatitis | Eosinophils | B-cells followed by IgE |
| (Eczema) | T-Cells | mediated activation of |
| Allergic Rhinitis | B-Cells | resident Mast cells and Eosinophils |
| Cell Mediated Hypersensitivity | | |
| Allergic Contact Dermatitis | T-cells | T-cell hypersensitivity |
| Hypersensitivity Pneumonitis | B-cells | |
| Rheumatic Diseases | | |
| Systemic Lupus Erythematosus (SLE) | Monocytes | Cytokine Production (e.g.TNF, IL-1, CSF-1, GM-CSF) |
| Rheumatoid Arthritis | Macrophages Neutrophils | |
| Juvenile Arthritis | Mast Cells | T-cell Activation |
| Sjögren's Syndrome | Eosinophils | JAK/STAT activation |
| Scleroderma | T-Cells | |
| Polymyositis | B-Cells | |
| Ankylosing Spondylitis | | |
| Psoriatic Arthritis | | |
| Viral Diseases | | |
| Epstein Barr Virus (EBV) | Lymphocytes | JAK/STAT Activation |
| Hepatitis B | Hepatocytes | JAK/STAT Activation |
| Hepatitis C | Hepatocytes | JAK/STAT Inhibition |
| HIV | Lymphocytes | JAK/STAT Activation |
| HTLV 1 | Lymphocytes | JAK/STAT Activation |
| Varicella-Zoster Virus (VZV) | Fibroblasts | JAK/STAT Inhibition |
| Human Papilloma Virus (HPV) | Epithelial cells | JAK/STAT Inhibition |
| Cancer | | |
| Leukemia | Leucocytes | Cytokine production |
| Lymphoma | Lymphocytes | JAK/STAT Activation |
| Neurodegenerative Diseases | | |
| Motor Neuron Disease | Neurons | Mutated SOD1 |
| Cardiovascular Diseases | | |
| Atherosclerosis & Arteriosclerosis | Lymphocytes | JAK/STAT Activation |
| | Macrophages | JAK/STAT Activation |
| | Myoepithelial cells | |
| Cardiac Hypertrophy | Cardiac Myocytes | JAK/STAT Activation |
| Ischemia | Cardiac Myocytes | JAK/STAT Activation |
| Pulmonary Hypertension | Lung Epithelium | JAK/STAT Activation |

TABLE 2

Diseases Potentially Treatable By JAK-Based Drug Therapies

| Target Disease | Cytokine | JAK family member | Strength of Association |
|---|---|---|---|
| Asthma | IL-4 & IL-9 | JAK1 & JAK3 | +++ |
| | IL-13 | JAK1 & JAK2 | +++ |
| | IL-5 | JAK2 | +++ |
| Eczema | IL-4 | JAK1 & JAK3 | +++ |
| | IFN-α | JAK1 & JAK2 | +++ |
| Food Allergy | IL-4 | JAK1 & JAK3 | +++ |

TABLE 2-continued

Diseases Potentially Treatable By JAK-Based Drug Therapies

| Target Disease | Cytokine | JAK family member | Strength of Association |
|---|---|---|---|
| Inflammatory Bowel Disease & Crohn's Disease | IL-4 | JAK1 & JAK3 | +++ |
| Leukaemia And Lymphoma | (IL-2) | JAK3, JAK1 & JAK2 | +++ |
| Cutaneous Inflammation | GM-CSF & IL-6 | JAK1 & JAK2 | +++ |
| Immune Suppression By Solid Tumour | IL-10 | JAK1 & TYK2 | +++ |
| Prostate Cancer | IL-6 | JAK1, JAK2 & Tyk2 | +++ |
| Atherosclerosis & arteriosclerosis | Various Cytokines | JAK3 | ++ |
| Cardiac Hypertrophy | Angiotensin II | JAK2 | +++ |

SUMMARY OF THE INVENTION

The present inventors have found that a group of compounds based upon the disubstituted pyrazine scaffold I, are inhibitors of tyrosine kinases.

Accordingly, in a first aspect the present invention provides a compound of the general formula

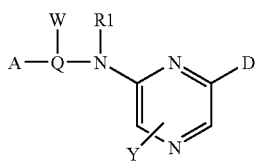

I or pharmaceutically acceptable prodrugs, salts, hydrates, solvates, crystal forms or diastereomers thereof, wherein:

D is a heterocyclic ring selected from:

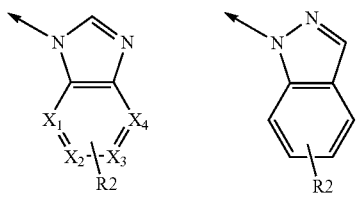

where $X_1$, $X_2$, $X_3$, $X_4$ are optionally substituted carbon, or one of $X_1$, $X_2$, $X_3$, $X_4$ is nitrogen and the rest are optionally substituted carbon;

R2 is 0-3 substituents independently chosen from H, halogen, $C_{1-4}$ alkyl, $CF_3$, $OCF_3$, $OCHF_2$, CN, aryl, hetaryl, $C_{1-4}$ alkylOH, $C_{1-4}$alkylNR3R4, $C_{1-4}$alkylhetaryl, $OC_{1-4}$alkyl, $OC_{1-4}$alkylNR3R4, $OC_{1-4}$alkylhetaryl, $OC_{1-4}$alkylOH, $CO_2$R3, CONR3R4, NR3R4, nitro, NR3COR4, NR5CONR3R4, NR3SO$_2$R4, $C_{1-4}$alkylNR3COR4, $C_{1-4}$alkylNR5CONR3R4, $C_{1-4}$alkylNR3SO$_2$R4;

R3, R4 are each independently H, $C_{1-4}$ alkyl, $C_{1-4}$alkyl OH, $C_{1-4}$alkylNR19R20, $C_{1-4}$ alkyl cycloalkyl, $C_{1-4}$ cyclohetalkyl, aryl, $C_{1-4}$ alklylaryl, hetaryl, $C_{1-4}$ alkylhetaryl, or may be joined to form an optionally substituted 3-8 membered (saturated or unsaturated) ring optionally containing an atom selected from O, S, NR6;

and R5 is selected from H, $C_{1-4}$ alkyl, aryl or hetaryl;

R6 is selected from H, $C_{1-4}$ alkyl, $C_{1-4}$alkyNR19R20, aryl, hetryl, $C_{1-4}$ alkyl aryl, $C_{1-4}$ alkyl hetaryl;

R19, R20 are each independently selected from H, $C_{1-4}$alkyl;

R1 is H, $C_{1-4}$ alkyl, $C_{1-6}$cycloalkyl, or may form a 5-8 membered ring onto the ortho position of ring A;

Q is a bond, $CH_2$, $C_{1-4}$ alkyl;

A is aryl, hetaryl optionally substituted with 0-3 substituents independently chosen from halogen, $C_{1-4}$ alkyl, $CF_3$, $OCF_3$, CN, NR8R9, aryl, hetaryl, $C_{1-4}$aryl, $C_{1-4}$hetaryl, $C_{1-4}$ alkylNR8R9, $OC_{1-4}$ alkylNR8R9, nitro, NR10C$_{1-4}$NR8R9, NR8COR9, NR10CONR8R9, NR8SO$_2$R9, CONR8R9, CO$_2$R8;

R8 and R9 are each independently H, $C_{1-4}$ alkyl aryl or together form an optionally substituted 4-8 membered ring which may contain a heteroatom selected from O, S, NR11;

R10 is selected from H, $C_{1-4}$ alkyl;

R11 is selected from H, $C_{1-4}$alkyl;

W is selected from H, $C_{1-4}$alkyl, $C_{2-6}$alkenyl or may form a 5-8 membered ring onto the ortho position of ring A; where $C_{1-4}$alkyl or $C_{2-6}$alkenyl may be optionally substituted with $C_{1-4}$alkyl, OH, $OC_{1-4}$alkyl, NR12R13;

R12, and R13 are each independently H, $C_{1-4}$alkyl, or may be joined to form an optionally substituted 3-8 membered ring optionally containing an atom selected from O, S, NR14;

R14 is selected from H, $C_{1-4}$alkyl;

Y is 0-2 substituents selected from H, $C_{1-4}$ alkyl, NR15R16;

R15 and R16 are independently selected from H, $C_{1-4}$alkyl.

In a second aspect the present invention provides a composition comprising a carrier and at least one compound of the first aspect of the invention.

In a third aspect the present invention provides a method of treating a tyrosine kinase-associated disease state in a subject, the method comprising administering a therapeutically effective amount of at least one compound of the first aspect of the invention or a therapeutically effective amount of a composition of the second aspect of the invention.

DETAILED DESCRIPTION OF THE INVENTION

The present inventors have found that a group of compounds based upon the disubstituted pyrazine scaffold I, are inhibitors of tyrosine kinases.

Accordingly, in a first aspect the present invention provides a compound of the general formula

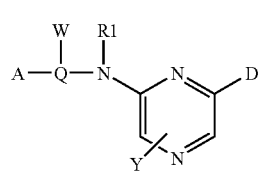

I or pharmaceutically acceptable prodrugs, salts, hydrates, solvates, crystal forms or diastereomers thereof, wherein:

D is a heterocyclic ring selected from:

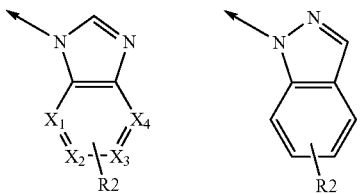

where $X_1, X_2, X_3, X_4$ are optionally substituted carbon, or one of $X_1, X_2, X_3, X_4$ is nitrogen and the rest optionally substituted carbon;

R2 is 0-3 substituents independently chosen from H, halogen, $C_{1-4}$ alkyl, $CF_3$, $OCF_3$, $OCHF_2$, CN, aryl, hetaryl, $C_{1-4}$ alkylOH, $C_{1-4}$alkylNR3R4, $C_{1-4}$alkylhetaryl, $OC_{1-4}$alkyl, $OC_{1-4}$alkylNR3R4, $OC_{1-4}$alkylhetaryl, $OC_{1-4}$alkylOH, $CO_2R3$, CONR3R4, NR3R4, nitro, NR3COR4, NR5CONR3R4, NR3SO$_2$R4, $C_{1-4}$alkylNR3COR4, $C_{1-4}$alkylNR5CONR3R4, $C_{1-4}$alkylNR3SO$_2$R4;

R3, R4 are each independently H, $C_{1-4}$alkyl $C_{1-4}$alkyl OH, $C_{1-4}$alkylNR19R20, $C_{1-4}$ alkyl cycloalkyl, $C_{1-4}$ cyclohetalkyl, aryl, $C_{1-4}$ alklylaryl, hetaryl, $C_{1-4}$ alkylhetaryl, or may be joined to form an optionally substituted 3-8 membered (saturated or unsaturated) ring optionally containing an atom selected from O, S, NR6;

and R5 is selected from H, $C_{1-4}$ alkyl, aryl or hetaryl;
R6 is selected from H, $C_{1-4}$ alkyl, $C_{1-4}$alkylNR19R20, aryl, hetaryl, $C_{1-4}$ alkyl aryl, $C_{1-4}$ alkyl hetaryl;
R19, R20 are each independently selected from H, $C_{1-4}$alkyl;

R1 is H, $C_{1-4}$ alkyl, $C_{1-6}$ cycloalkyl, or may form a 5-8 membered ring onto the ortho position of ring A;

Q is a bond, $CH_2$, $C_{1-4}$ alkyl;

A is aryl, hetaryl optionally substituted with 0-3 substituents independently chosen from halogen, $C_{1-4}$ alkyl, $CF_3$, $OCF_3$, CN, NR8R9, aryl, hetaryl, $C_{1-4}$aryl, $C_{1-4}$hetaryl, $C_{1-4}$ alkylNR8R9, $OC_{1-4}$alkylNR8R9, nitro, NR10$C_{1-4}$NR8R9, NR8COR9, NR10CONR8R9, NR8SO$_2$R9, CONR8R9, $CO_2R8$;

R8 and R9 are each independently H, $C_{1-4}$ alkyl, aryl or together form an optionally substituted 4-8 membered ring which may contain a heteroatom selected from O, S, NR11;
R10 is selected from H, $C_{1-4}$ alkyl;
R11 is selected from H, $C_{1-4}$ alkyl;

W is selected from H, $C_{1-4}$alkyl, $C_{2-6}$alkenyl or may form a 5-8 membered ring onto the ortho position of ring A; where $C_{1-4}$alkyl or $C_{2-6}$alkenyl may be optionally substituted with $C_{1-4}$alkyl, OH, $OC_{1-4}$alkyl, NR12R13;

R12, and R13 are each independently H, $C_{1-4}$alkyl, or may be joined to form an optionally substituted 3-8 membered ring optionally containing an atom selected from O, S, NR14;
R14 is selected from H, $C_{1-4}$ alkyl;

Y is 0-2 substituents selected from H, $C_{1-4}$alkyl, NR15R16;
R15 and R16 are independently selected from H, $C_{1-4}$alkyl.

In the above description it will be appreciated that:
$C_{1-4}$alkyl means a straight or branched alkyl chain.

Aryl means phenyl or naphthyl.
Hetaryl means a 5- or 6-membered heteroaromatic ring containing one or more heteroatoms selected from O, N, S.
Cycloalkyl means a 3-8 membered saturated ring
Cyclohetalkyl means a 3-8 membered saturated ring containing 1-3 heteroatoms selected from O, S, NR17, where R17 is H, $C_{1-4}$ alkyl, aryl, hetaryl.

In a further preferred embodiment the compound is selected from compounds of the general formula II.

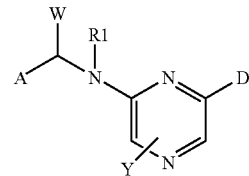

II or pharmaceutically acceptable prodrugs, salts, hydrates, solvates, crystal forms or diastereomers thereof, wherein:

D is a heterocyclic ring selected from:

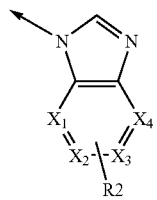

where $X_1, X_2, X_3, X_4$ are optionally substituted carbon, or one of $X_1, X_2, X_3, X_4$ is N and the rest optionally substituted carbon;

R2 is 0-3 substituents independently chosen from H, halogen, $C_{1-4}$alkyl, $CF_3$, $OCF_3$, $OCHF_2$, CN, aryl, hetaryl, $C_{1-4}$ alkylOH, $C_{1-4}$alkylNR3R4, $C_{1-4}$alkylhetaryl, $OC_{1-4}$ alkyl, $OC_{1-4}$alkylNR3R4, $OC_{1-4}$alkylhetaryl, $OC_{1-4}$alkylOH, $CO_2R3$, CONR3R4, NR3R4, nitro, NR3COR4, NR5CONR3R4, NR3SO$_2$R4, $C_{1-4}$alkylNR3COR4, $C_{1-4}$alkylNR5CONR3R4, $C_{1-4}$alkylNR3SO$_2$R4;

R3, R4 are each independently H, $C_{1-4}$ alkyl, $C_{1-4}$alkyl OH, $C_{1-4}$alkylNR19R20, $C_{1-4}$ alkyl cycloalkyl, $C_{1-4}$ cyclohetalkyl, aryl, $C_{1-4}$ alkylaryl, hetaryl, $C_{1-4}$ alkyl hetaryl, or may be joined to form an optionally substituted 3-8 membered (saturated or unsaturated) ring optionally containing an atom selected from O, S, NR6;

and R5 is selected from H, $C_{1-4}$ alkyl, aryl or hetaryl;
R6 is selected from H, $C_{1-4}$alkyl, $C_{1-4}$alkylNR19R20, aryl, hetaryl, $C_{1-4}$ alkyl aryl, $C_{1-4}$ alkyl hetaryl;
R19, R20 are each independently selected from H, $C_{1-4}$alkyl;

R1 is H, $C_{1-4}$ alkyl, $C_{1-6}$ cycloalkyl, or may form a 5-8 membered ring onto the ortho position of ring A;

A is aryl, hetaryl optionally substituted with 0-3 substituents independently chosen from halogen, $C_{1-4}$ alkyl, $CF_3$, $OCF_3$, CN, NR8R9, aryl, hetaryl, $C_{1-4}$aryl, $C_{1-4}$hetaryl, $C_{1-4}$ alkylNR8R9, $OC_{1-4}$alkylNR8R9, nitro, NR10$C_{1-4}$NR8R9, NR8COR9, NR10CONR8R9, NR8SO$_2$R9, CONR8R9, $CO_2R8$;

R8 and R9 are each independently H, $C_{1-4}$ alkyl, aryl or together form an optionally substituted 4-8 membered ring which may contain a heteroatom selected from O, S, NR11;

R10 is selected from H, $C_{1-4}$alkyl;

R11 is selected from H, $C_{1-4}$alkyl;

W is selected from H, $C_{1-4}$alkyl, $C_{2-6}$alkenyl or may form a 5-8 membered ring onto the ortho position of ring A; where $C_{1-4}$alkyl or $C_{2-6}$alkenyl may be optionally substituted with $C_{1-4}$-alkyl, OH, $OC_{1-4}$alkyl, NR12R13;

R12, and R13 are each independently H, $C_{1-4}$-alkyl, or may be joined to form an optionally substituted 3-8 membered ring optionally containing an atom selected from O, S, NR14;

R14 is elected from H, $C_{1-4}$ alkyl;

Y is 0-2 substituents selected from H, $C_{1-4}$ alkyl, NR15R16;

R15 and R16 are independently selected from H, $C_{1-4}$alkyl.

In the above description it will be appreciated that:

$C_{1-4}$alkyl means a straight or branched alkyl chain.

Aryl means phenyl or naphthyl.

Hetaryl means a 5- or 6-membered heteroaromatic ring containing one or more heteroatoms selected from O, N, S.

Cycloalkyl means a 3-8 membered saturated ring

Cyclohetalkyl means a 3-8 membered saturated ring containing 1-3 heteroatoms selected from O, S, NR17, where R17 is H, $C_{1-4}$ alkyl, aryl, hetaryl.

The compounds of this invention include all conformational isomers (eg. cis and trans isomers). The compounds of the present invention have asymmetric centers and therefore exist in different enantiomeric and diastereomeric forms. This invention relates to the use of all optical isomers and stereoisomers of the compounds of the present invention, and mixtures thereof, and to all pharmaceutical compositions and methods of treatment that may employ or contain them. In this regard, the invention includes both the E and Z confirmations. The compounds of formula I may also exist as tautomers. This invention relates to the use of all such tautomers and mixtures thereof.

This invention also encompasses pharmaceutical compositions containing prodrugs of compounds of the formula I. This invention also encompasses methods of treating or preventing disorders in a subject that can be treated or prevented by the inhibition of protein kinases, such as JAK comprising administering prodrugs of compounds of the formula I. Compounds of formula I having free amino, amido, hydroxy or carboxylic groups can be converted into prodrugs. Prodrugs include compounds wherein an amino acid residue, or a polypeptide chain of two or more (eg, two, three or four) amino acid residues which are covalently joined through peptide bonds to free amino, hydroxy and carboxylic acid groups of compounds of formula I. The amino acid residues include the 20 naturally occurring amino acids commonly designated by three letter symbols and also include, 4-hydroxyproline, hydroxylysine, demosine, isodemosine, 3-methylhistidine, norvlin, beta-alanine, gamma aminobutyric acid, citrulline, homocysteine, homoserine, ornithine and methionine sulfone. Prodrugs also include compounds wherein carbonates, carbamates, amides and alkyl esters which are covalently bonded to the above substituents of formula I through the carbonyl carbon prodrug sidechain. Prodrugs also include phosphate derivatives of compounds of formula I (such as acids, salts of acids, or esters) joined through a phosphorus-oxygen bond to a free hydroxyl of compounds of formula I.

In a still further preferred embodiment the compound possesses S chirality at the chiral carbon bearing W, where W is $C_{1-4}$ alkyl. The compound can be used as a purified isomer or as a mixture of any ratio of isomers. It is however preferred that the mixture comprises at least 70%, 80%; 90%, 95%, or 99% of the preferred isomer.

In a second aspect the present invention provides a composition comprising a carrier and at least one compound of the first aspect of the invention.

In a third aspect the present invention provides a method of treating a tyrosine kinase-associated disease state in a subject, the method comprising administering a therapeutically effective amount of at least one compound of the first aspect of the invention or a therapeutically effective amount of a composition of the second aspect of the invention.

In a further preferred embodiment the disease state involves JAK1, JAK2, JAK3 or TYK2.

In a preferred embodiment of the present invention the disease state is selected from the group consisting of Atopy, such as Allergic Asthma, Atopic Dermatitis (Eczema), and Allergic Rhinitis; Cell Mediated Hypersensitivity, such as Allergic Contact Dermatitis and Hypersensitivity Pneumonitis; Rheumatic Diseases, such as Systemic Lupus Erythematosus (SLE), Rheumatoid Arthritis, Juvenile Arthritis, Sjögren's Syndrome, Scleroderma, Polymyositis, Ankylosing Spondylitis, Psoriatic Arthritis; Other autoimmune diseases such as Type I diabetes, autoimmune thyroid disorders, and Alzheimer's disease; Viral Diseases, such as Epstein Barr Virus (EBV), Hepatitis B, Hepatitis C, HIV, HTLV 1, Varicella-Zoster Virus (VZV), Human Papilloma Virus (HPV); Cancer, such as Leukemia, Lymphoma and Prostate Cancer; Neurodegenerative Diseases such as Motor Neuron Disease; Cardiovascular Diseases such as Cardiac Hypertrophy, Ischemia, Pulmonary Hypertension, Atherosclerosis and Arteriosclerosis.

As used herein the term "tyrosine kinase-associated disease state" refers to those disorders which result from aberrant tyrosine kinase activity, in particular JAK activity and/or which are alleviated by inhibition of one or more of these enzymes.

In further aspects the present invention provides the use of the compounds described in the preparation of medicaments for the treatment of JAK-associated disease states.

As used herein the term "JAK", "JAK kinase" or "JAK family" refers to protein tyrosine kinases which possess the characterizing features of JAK1, JAK2, JAK3 and TYK as described herein.

The present invention provides pharmaceutical compositions comprising at least one of the compounds of the present invention capable of treating a JAK-associated disorder in an amount effective therefore and a pharmaceutically acceptable vehicle or diluent. The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the present invention may be administered by any suitable means, for example, orally, such as in the form of tablets, capsules, granules or powders, sublingually; buccally; parenterally, such as by subcutaneous, intravenous, intramuscular, or intracisternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The compound may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The compounds may also be administered liposomally.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

Diseases and conditions associated with inflammation and infection can be treated using the method of the present invention. In a preferred embodiment, the disease or condition is one in which the actions of eosinophils and/or lymphocytes are to be inhibited or promoted, in order to modulate the inflammatory response.

The subjects treated in the above methods, in whom which JAK inhibition is desired, are mammals, including, but not limited to, cows, sheep, goats, horses, dogs, cats, guinea pigs, rats or other bovine, ovine, equine, canine, feline, rodent or murine species, and preferably a human being, male or female.

The term "therapeutically effective amount" means the amount of the subject composition that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention to the individual in need of treatment.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation produces of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an antioxidant such as ascorbic acid.

Dispersible powders and granules suitable for preparation of all aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol hydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles.)

The compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolisable lipid capable of forming liposomes can be used. The present compositions in liposome form can contain, in addition to a compound of the present invention, stabilisers, preservatives, excipients and the like. The preferred lipids are the phospholipids and phosphatidyl cholines, both natural and synthetic. Methods to form liposomes are known in the art.

The pharmaceutical composition and method of the present invention may further comprise other therapeutically active compounds as noted herein which are usually applied in the treatment of the above mentioned pathological conditions. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

Examples of other therapeutic agents include the following:

cyclosporins (e.g., cyclosporin A), CTLA4-Ig, antibodies such as ICAM-3, anti-IL-2 receptor (Anti-Tac), anti-CD45RB, anti-CD2, anti-CD3 (OKT-3), anti-CD4, anti-CD80, anti-CD86, agents blocking the interaction between CD40 and gp39, such as antibodies specific for CD40 and/or gp39 (i.e., CD154) fusion proteins constructed from CD40 and gp39 (CD40Ig and CD8gp39), inhibitors, such as nuclear translocation inhibitors, of NP-kappa B function, such as deoxyspergualin (DSG), cholesterol biosynthesis inhibitors such as HMG CoA reductase inhibitors (lovastatin and simvastatin), non-steroidal antiinflammatory drugs (NSAIDs) such as ibuprofen, aspirin, acetaminophen and cyclooxygenase inhibitors such as rofecoxib, steroids such as prednisolone or dexamethaone, gold compound, antiproliferative agents such as methotrexate, FK506 (tacrolimus, Prograf), mycophenolate mofetil, cytotoxic drugs such as azathioprine, VP-16, etoposide, fludarabine, cisplatin and cyclophosphamide, TNF-11 inhibitors such as tenidap, anti-TNF antibodies or soluble TNF receptor, and rapamycin (sirolimus or Rapamune) or derivatives thereof.

When other therapeutic agents are employed in combination with the compounds of the present invention they may be used for example in amounts as noted in the Physician Desk Reference (PDR) or as otherwise determined by one of ordinary skill in the art.

In the treatment or prevention of conditions; which require protein tyrosine kinase inhibition an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

All publications mentioned in this specification are herein incorporated by reference.

Any discussion of documents, acts, materials, devices, articles or the like which has been included in the present specification is solely for the purpose of providing a context for the present invention. It is not to be taken as an addition that any or all of these matters form part of the prior art base or were common general knowledge in the field relevant to the present invention as it existed in Australia before the priority date of each claim of this application.

In order that the nature of the present invention may be more clearly understood preferred forms thereof will now be described by reference to the following non-limiting Examples.

EXAMPLES

Materials and Methods

Compound Synthesis

Compounds are generally prepared in a 2-step process starting from 2,6-dichloropyrazine.

The first step is a nucleophilic aromatic substitution to generate a monoamino-monohalo intermediate. (Scheme 1)

Scheme 1

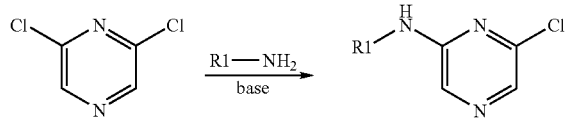

The nucleophilic aromatic substitution is typically carried out by addition of a primary amine to the di-halogenated heterocycle in a solvent such as ethanol, isopropanol, tert-butanol, dioxane, THF, DMF, toluene or xylene. The reaction is typically performed at elevated temperature in the presence of excess amine or a non-nucleophilic base such as trimethylamine or diisopropylethylamine, or an inorganic base such as potassium carbonate or sodium carbonate.

Alternatively, the amino substituent may be introduced through a transition metal catalysed amination reaction. Typical catalyst systems for such transformations include Pd(OAc)$_2$/P(t-Bu)$_3$, Pd$_2$(dba)$_3$/BINAP and Pd(OAc)$_2$/BINAP.

The amines employed in the first step of the synthesis of these compounds are obtained commercially or are prepared using methods well known to those skilled in the art. Of particular interest are α-methylbenzylamines which are obtained commercially or may be prepared through reduction of oximes (Scheme 2). Typical reductants include lithium aluminium hydride, hydrogen gas in the presence of catalytic palladium on charcoal, Zn in the presence of hydrochloric acid, sodium borohydride in the presence of a Lewis acid such as TiCl$_3$, ZrCl$_4$, NiCl$_2$ and MoO$_3$, or sodium borohydride in conjunction with Amberlyst H15 ion exchange resin and LiCl. The oximes are obtained in one-step from the corresponding ketones through condensation with hydroxylamine. This reaction is generally performed in a protic solvent such as water or ethanol, at temperatures from 0° C. to reflux. The hydroxylamine is generally used in the form of its hydrochloride salt, and therefore the reaction is performed in the presence of a base such as sodium hydroxide. The ketones employed as starting materials are generally obtained commercially or via procedures well known to those skilled in the art.

Scheme 2

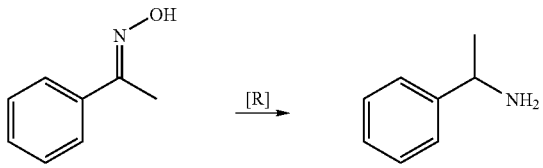

α-Methyl benzylamines of high optical purity nay be prepared from chiral α-methyl benzyl alcohols using methods well known to those skilled in the art. Such methods include derivatisation of the hydroxyl as a mesylate or tosylate and displacement with a nitrogen nucleophile, such as phthalimide or azide which can then converted to the primary amine using conventional synthetic methods; or, displacement of the hydroxyl with a suitable nitrogen nucleophile under Mitsunobu conditions. The dial α-methyl benzyl alcohols may be obtained through chiral reduction of the corresponding ketones. Chiral reducing methods are now well known in organic chemistry and include enzymatic processes, asymmetric hydrogenation procedures and chiral oxazaborolidines.

The second step of the synthesis involves a nucleophilic aromatic substitution reaction of the monochloro-mono-amino pyrazine with benzimidazole or indazole. The reaction is typically performed using a salt of the benzimidazole or indazole in solvents such as tetrahydrofuran, dimethylformamide, toluene, or xylene from room temperature to reflux. The benzimidazole or indazole salt is prepared by reaction with a metal hydride such as sodium or potassium hydride or by reaction with caesium carbonate. Alternatively, a metal-catalysed coupling reaction can be used to introduce the benzimidazole or indazole ring. The reaction is typically performed using a base such as caesium carbonate, rubidium carbonate, potassium carbonate, sodium tert-butoxide or potassium phosphate in a solvent such as xylene, toluene, and DMF from room temperature to reflux. Auxiliary reagents such as phase transfer agents (e.g. cetrimonium bromide) or copper complexing agents (e.g. phenanthroline) may also be employed in the reaction.

The benzimidazole or indazole components used in this reaction are obtained commercially or are prepared from commercially available benzimidazoles or indazoles via techniques well known to those skilled in the art.

Alternatively, a benzimidazole or indazole derivative may be reacted with the mono-amino mono-chloro pyrazine and the subsequent product further derivatised using methods well known to those skilled in the art.

Representative syntheses are reported below.

Example 1

6-Chloro-N-[(1S)-1-(4-fluorophenyl)ethyl]pyrazin-2-amine

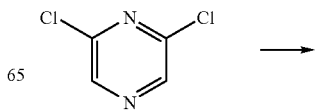

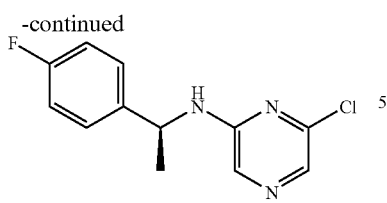

A solution of S-(−)-1-(4-fluorophenyl)-ethylamine (5.0 g, 35.9 mmol), 2,6-dichloropyrazine (5.90 g, 39.6 mmol), diisopropylethylamine (12.5 mL, 71.8 mmol) in ethoxyethanol (25 mL) was heated at 135° C. under N₂ overnight. The solvent was removed in vacuo and the residue washed with H₂O (2×30 mL) and dried (Na₂SO₄). The solvent was removed under reduced pressure and the residue triturated with hexanes (2×10 mL) to give a light brown solid. The washings were combined, concentrated and the residue obtained chromatographed using ethyl acetate-hexane (1:4-1:2) to separate solid product which, combined with the original solids, gave the total product (7.07 g, 78%).

$^1$H-n.m.r. (CDCl$_3$) δ 1.56 (d, 3H, J=6.8 Hz, CH$_3$), 4.81-4.94 (m, 1H, CH), 5.05 (m, 1H, NH), 6.98-7.07 (m, 2H, ArH), 7.29-7.36 (m, 2H, ArH), 7.60 (s, 1H, pyraz-H), 7.80 (s, 1H, pyraz-H).

Example 2

6-(1H-Benzimidazol-1-yl)-N-benzylpyrazin-2-amine

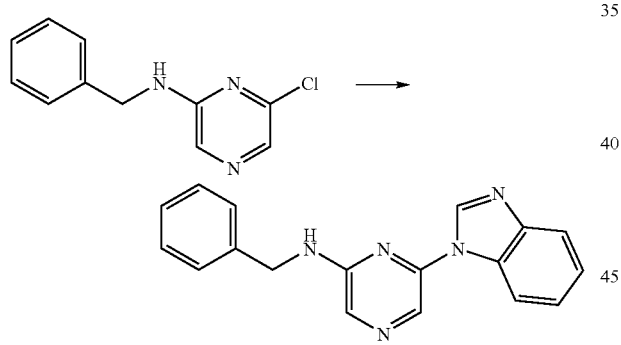

To a stirred solution of benzimidazole (130 mg, 1.1 mmol) in anhydrous DMF (5 mL) at 0° C. under N$_2$ was added sodium hydride (56 mg, 60% dispersion in oil, 1.45 mmol) in portions over 2 min. The mixture was stirred at 0° C. for 15 min and at RT for 60 min. To this was added a solution of (6-chloro-pyrazin-2-yl)-(1-benzyl)-amine (220 mg) in DMF (5 mL) and the resulting mixture was then heated at reflux for 18 h. The DMF was removed under reduced pressure and the residue diluted with chloroform. The organic layer was washed with water, dried (Na$_2$SO$_4$) and the solvent removed under reduced pressure to furnish the crude product. Column chromatography using dichloromethane-methanol (20:1→10:1) as eluant separated the product (100 mg).

$^1$H-n.m.r. (CDCl$_3$) δ 4.66 (d, 2H, J=5.7 Hz, CH$_2$), 5.56 (m, 1H, NH), 7.29-7.39 (m, 7H, ArH), 7.78-7.89 (m, 2H, ArH), 7.92 (1H, pyraz-H), 8.16 (s, 1H, pyraz-H, 8.48 (s, 1H, ArH2).

m/z (ES) 302 (M⁺+H).

Example 3

1-(6-Chloropyrazin-2-yl)-1H-benzimidazole-5-carboxamide and 1-(6-chloropyrazin-2-yl)-1H-benzimidazole-6-carboxamide

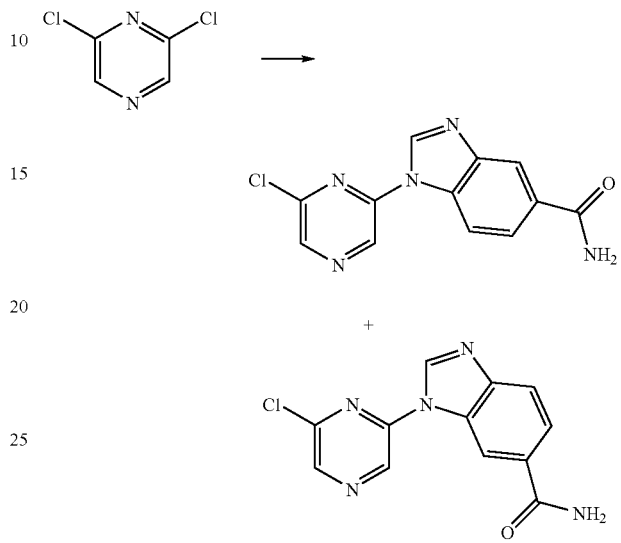

A mixture of 2,6-dichloropyrazine (2.0 g, 13.4 mmol), 1H-benzimidazole-5-carboxamide (2.0 g, 12.3 mmol) and cesium carbonate (5.6 g, 17.2 mmol) in DMF (10 mL) was heated at 90° C. for 3 h. The solution was cooled to RT and diluted with ethyl acetate (20 mL) and filtered. The solid material was washed with chloroform-methanol (20 mL, 4:1) and the combined filtrates concentrated in vacuo. The residue thus obtained (3.02 g) was used without further purification.

m/z (EI) 273/275 (M+1)

Example 4

1-(6-Chloropyrazin-2-yl)-1H-benzimidazole-5-carbonitrile and 1-(6-chloropyrazin-2-yl)-1-benzimidazole-6-carbonitrile

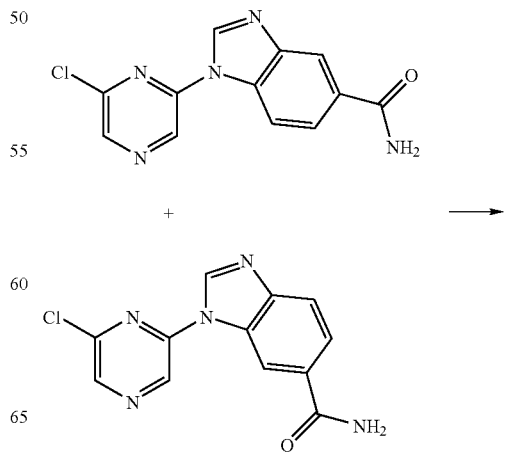

-continued

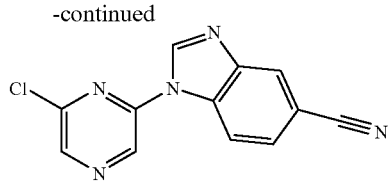

+

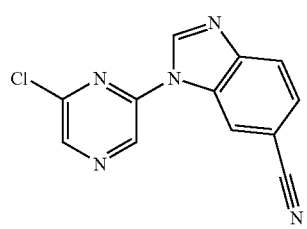

An approximately 1:1 mixture of 1-(6-chloropyrazin-2-yl)-1H-benzimidazole-5-carboxamide and 1-(6-chloropyrazin-2-yl)-1H-benzimidazole-6-carboxamide (0.3 g, 1.09 mmol) and thionyl chloride (0.3 mL, 3.3 mmol) in benzene (3 mL) was heated under reflux overnight. Upon cooling to RT the solution was poured onto ice and the resultant mixture basified to pH ~11 with solid Na$_2$CO$_3$. The mixture was then extracted with ethyl acetate (2×20 mL) and the combined organic layers washed with brine and dried (Na$_2$SO$_4$). The solvent was removed in vacuo and the residue purified by column chromatography using dichloromethane-methanol (100:0-96:4) as eluant to give the desired product as a mixture of isomers (135 mg).

m/z (EI) 255/257 (M+1)

Example 5

6-(1H-Benzimidazol-1-yl)-N-[(1R)-1-phenylethyl]pyrazin-2-amine

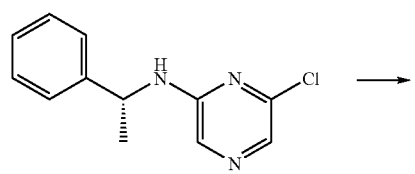

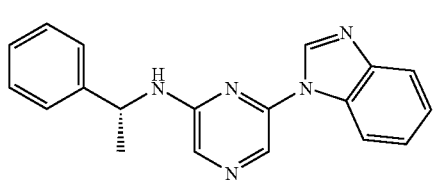

In a procedure analogous to example 2, reaction of 6-chloro-N-[(1R)-1-phenylethyl]pyrazin-2-amine (240 mg, 1.03 mmol) and benzimidazole (130 mg, 1.10 mmol) furnished the product (187 mg, 59%).

$^1$H-n.m.r. (CDCl$_3$) δ 1.63 (d, 3H, J=6.6 Hz, CH$_3$), 4.98-5.20 (m, 1H, CH), 5.58 (d, 1H, J=6.0 Hz, NH), 7.25-7.42 (m, 6H, Ph-H, ArH), 7.70 (dd, 1H, J=7.2, 1.0 Hz, ArH), 7.82 (dd, 1H, J=8.0, 1.2 Hz, ArH), 7.87 (s, 1H, pyraz-H), 8.11 (s, 1H, pyraz-H), 8.38 (s, 1H, ArH).

m/z (ES) 315 (M$^+$+H), 212, 105.

Example 6

6-(1H-Benzimidazol-1-yl)-N-[(1S)-1-phenylethyl]pyrazin-2-amine

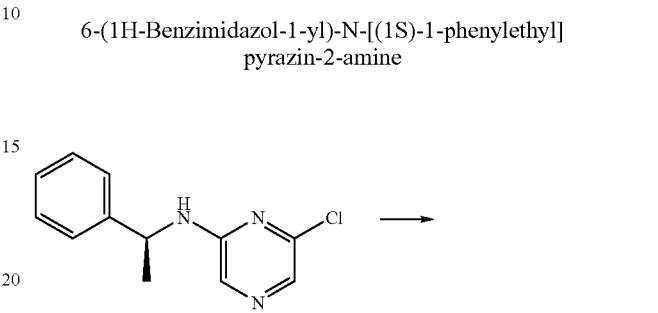

In a procedure analogous to example 2, reaction of 6-chloro-[(1S)-1-phenylethyl]pyrazin-2-amine (140 mg, 0.60 mmol) and benzimidazole (78 mg, 0.66 mmol) furnished the product (71 mg, 38%).

$^1$H-n.m.r. (CDCl$_3$) δ 1.57 (d, 3H, J=6.9 Hz, CH$_3$), 4.95 (m, 1H, CH); 5.29 (d, 1H, J=6.0 Hz, NH), 7.19-7.35 (m, 7H, Ph-H, ArH), 7.63-7.66 (m, 1H, ArH), 7.74-7.77 (m, 1H, ArH), 7.78 (s, 1H, pyraz-H), 8.06 (s, 1H, pyraz-H), 8.31 (s, 1H, ArH).

m/z (ES) 316 (M$^+$+H), 212, 105

Example 7

6-Chloro-N-methyl-N-[(1S)-1-phenylethyl]pyrazin-2-amine

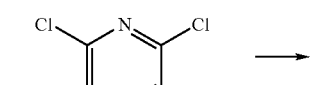

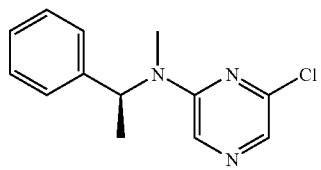

In an analogous fashion to example 1, N-methyl-N-[(1S)-1-phenylethyl]amine (0.27 g, 2.0 mmol) was condensed with 2,6-dichloropyrazine (0.36 g, 2.4 mmol), to furnish the desired product as a light brown solid (192 mg, 39%).

$^1$H-n.m.r. (CDCl$_3$) δ 1.56 (d, 3H, J=6.8 Hz, CH$_3$), 4.81-4.94 (m, 1H, CH), 5.05 (m, 1H, NH), 6.98-7.07 (m, 2H, ArH), 7.29-7.36 (m, 2H, ArH), 7.60 (s, 1H, pyraz-H), 7.80 (s, 1H, pyraz-H).

Example 8

1-(6-[[1-(3-Fluorophenyl)ethyl]amino]pyrazin-2-yl)-1H-benzimidazole-5-carboxamide and 1-(6-[[1-(3-Fluorophenyl)ethyl]amino]pyrazin-2-yl)-1H-benzimidazole-6-carboxamide

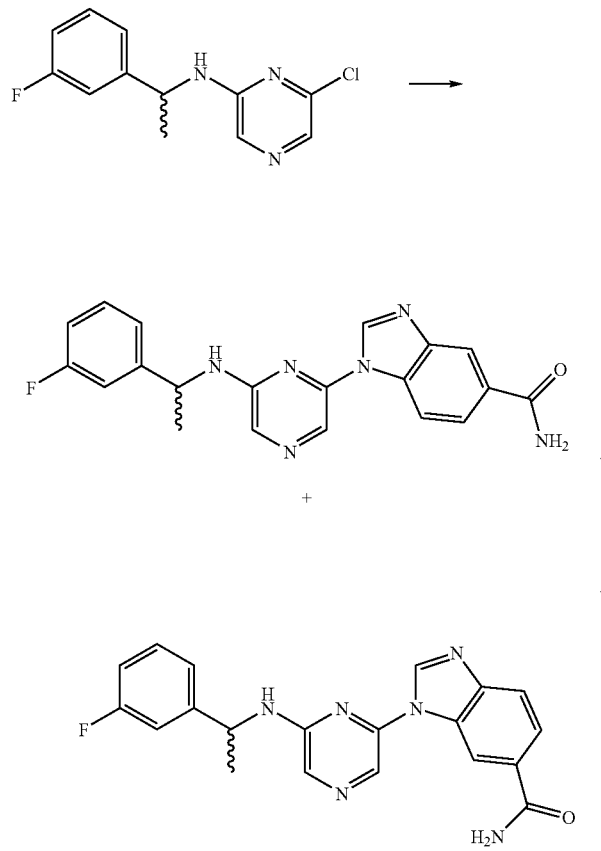

In an analogous fashion, to Example 3, 6-chloro-N-[1-(3-fluorophenyl)ethyl]pyrazin-2-amine (025 g, 1 mmol) was reacted with 1H-benzimidazole-5-carboxamide (0.2 g, 1.2 mmol) to afford the product as a mixture of isomers. These were separated by chromatography using dichloromethane-methanol (98:2-92:8) as eluant to afford from the less polar fractions 1-(6-{[1-(3-fluorophenyl)ethyl]amino}pyrazin-2-yl)-1H-benzimidazole-6-carboxamide (80 mg).

$^1$H-n.m.r. (CDCl$_3$) δ 1.64 (d, 3H, J=6.8 Hz, CH$_3$), 4.97-5.10 (m, 1H, CH), 5.47 (d, 1H, J=6.2 Hz, NH), 6.90-6.99 (m, 1H, ArH), 7.09-7.38 (m, 3H, ArH), 7.72 (dd, 1H, J=8.4, 1.6 Hz, ArH), 7.86 (s, 1H, pyraz-H), 7.87 (d, 1H, J=8.4 Hz, ArH), 8.22 (s, 1H, pyraz-H), 8.47 (s, 1H, ArH), 8.60 (d, 1H, J=1.6 Hz, ArH).

From the more polar fractions was isolated 1-(6-{[1-(3-fluorophenyl)ethyl]amino}pyrazin-2-yl)-1H-benzimidazole-5-carboxamide (63 mg).

$^1$H-n.m.r. (CDCl$_3$) δ 1.63 (d, 3H, J=6.8 Hz, CH$_3$), 4.94-5.07 (m, 1H, CH), 5.44 (d, 1H, J=6.6 Hz, NH), 6.90-7.38 (m, 4H, ArH), 7.65 (d, 1H, J=9.0 Hz, ArH), 7.82 (dd, 1H, J=8.8, 1.6 Hz, ArH), 7.93 (s, 1H, pyraz-H), 8.13 (s, 1H, pyraz-H), 8.25 (d, 1H, J=1.4 Hz, ArH), 8.41 (s, 1H, ArH),

Example 9

1-(6-[[1-(3-fluorophenyl)ethyl]amino]pyrazin-2-yl)-1H-benzimidazole-6-carbonitrile

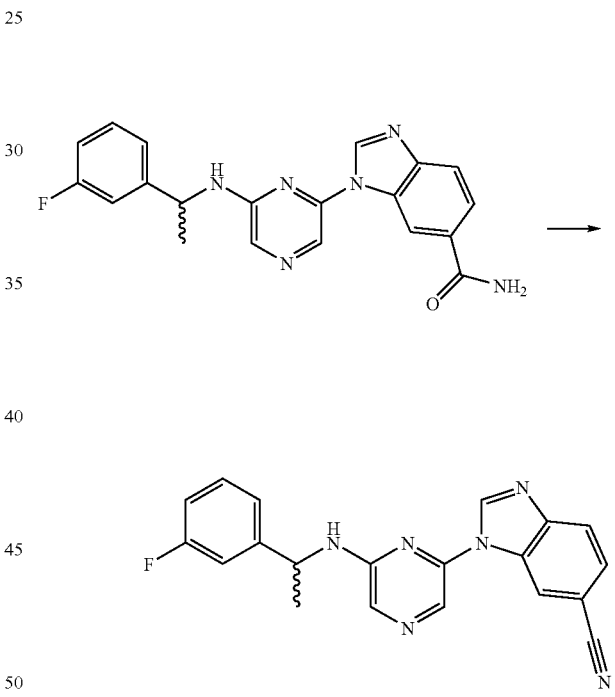

In an analogous procedure to that reported in Example 4, 1-(6-{[1-(3-fluorophenyl)ethyl]amino}pyrazin-2-yl)-1H-benzimidazole-6-carboxamide (83 mg 0.21 mmol) was reacted with phosphorus oxychloride to afford the product as a pale yellow solid (60 mg, 80%).

$^1$H-n.m.r. (CDCl$_3$) δ 1.65 (d, 3H, J=6.6 Hz, CH$_3$), 4.94-5.09 (m, 1H, CH), 5.57 (d, 1H, J=6.2 Hz, NH), 6.92-7.12 (m, 2H, ArH), 7.20-7.25 (m, 1H, ArH), 7.35-7.46 (m, 1H, ArH), 7.59 (dd, 1H, J=8.4, 1.4 Hz, ArH), 7.88 (d, 1H, J=8.4 Hz, ArH), 7.94 (s, 1H, pyraz-H), 8.12 (s, 1H, pyraz-H), 8.25 (d, 1H, J=1.4 Hz, ArH), 8.51 (s, 1H, ArH).

Example 10

1-[6-(3,4-Dihydroisoquinolin-2(1H)-yl)pyrazin-2-yl]-1H-benzimidazole-5-carbonitrile and 1-[6-(3,4-Dihydroisoquinolin-2(1H)-yl)pyrazin-2-yl]-1H-benzimidazole-6-carbonitrile

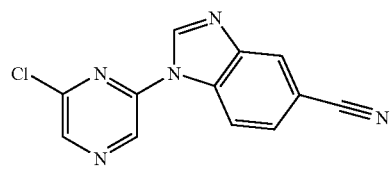

+

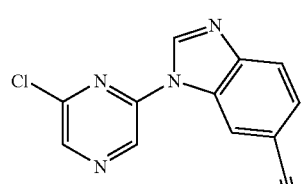

+

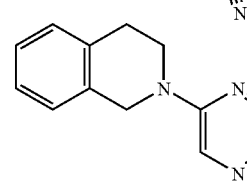

+

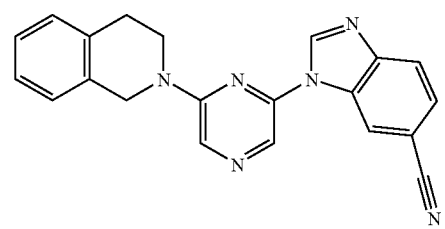

In an analogous fashion to Example 1, an approximately 1:1 mixture of 1-(6-chloropyrazin-2-yl)-1H-benzimidazole-5-carbonitrile and 1-(6-chloropyrazin-2-yl)-1H-benzimidazole-6-carbonitrile (102 mg, 0.4 mmol) was condensed with 1,2,3,4-tetrahydroisoquinoline (64 mg, 0.48 mol). The crude product was triturated with cold ethyl acetate to separate 1-[6-(3,4-dihydroisoquinolin-2(1H)-yl)pyrazin-2-yl]-1H-1-benzimidazole-5-carbonitrile as an off-white solid (65 mg)

$^1$H-n.m.r. (CDCl$_3$) δ 3.05-3.11 (m, 2H, CH$_2$), 3.95-4.02 (m, 2H, CH$_2$), 4.85 (m, 2H, CH$_2$), 7.25-7.29 (m, 3H, ArH), 7.61-7.68 (m, 1H, ArH), 7.95 (d, 1H, J=8.2 Hz, ArH), 8.11-8.21 (m, 1H, ArH), 8.16 (s, 1H, pyraz-H), 8.23 (s, 1H, pyraz-H), 8.38 (m, 1H, ArH), 8.65 (s, 1H, ArH).

The ethyl acetate washings were combined and concentrated in vacuo to furnish 1-[6-(3,4-dihydroisoquinolin-2(1H)-yl)pyrazin-2-yl]-1H-benzimidazole-6-carbonitrile (41 mg)

$^1$H-n.m.r. (CDCl$_3$) δ 3.07 (t, 2H, J=5.9 Hz, CH$_2$), 3.97 (t, 2H, J=6.1 Hz, CH$_2$), 4.84 (3, 2H, CH$_2$), 7.24-7.32 (m, 4H, ArH), 7.67 (dd, 1H, J=8.8, 1.4 Hz, ArH), 8.11-8.21 (m, 1H, ArH), 8.16 (s, 1H, pyraz-H), 8.22 (s, 1H, pyraz-H), 8.65 (s, 1H, ArH).

Example 11

1-(6-[(1S)-1,2,3,4-Tetrahydronaphthalen-1-ylamino]pyrazin-2-yl)-1H-benzimidazole-5-carbonitrile and 1-(6-[(1S)-1,2,3,4-Tetrahydronaphthalen-1-ylamino]pyrazin-2-yl)-1H-benzimidazole-6-carbonitrile

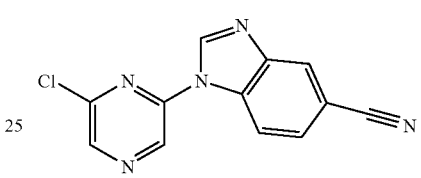

+

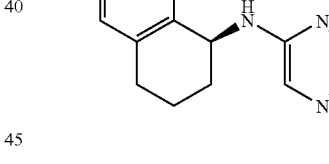

+

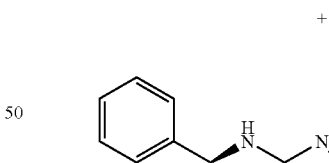

+

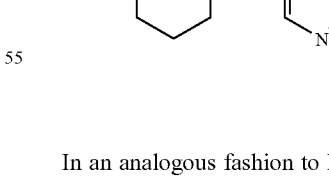

In an analogous fashion to Example 1, an approximately 1:1 mixture of 1-(6-chloropyrazin-2-yl)-1H-benzimidazole-5-carbonitrile and 1-(6-chloropyrazin-2-yl)-1H-benzimidazole-6-carbonitrile (100 mg, 0.39 mmol) was condensed with (1S)-1,2,3,4-tetrahydronaphthalen-1-amine (69 mg, 0.47 mmol). The product was obtained as a mixture of regioisomers which were separated by column chromatography using dichloromethane-methanol (95:5) as eluant. From the less polar fractions 1-{6[(1S)-1,2,3,4-tetrahydronaphthalen-1- ylamino]pyrazin-2-yl}-1H-benzimidazole-6-carbonitrile was obtained as a yellow semi-solid (26 mg).

¹H-n.m.r. (CDCl₃) δ 1.87-1.98 (m, 2H, CH₂), 2.04-2.18 (m, 2H, CH₂), 2.82-2.90 (m, 2H, CH₂), 5.18-5.30 (m, 2H, NH+CH), 7.14-7.23 (m, 3H, ArH), 7.32-7.38 (m, 1H, ArH), 7.61 (dd, 1H, J=8.2, 1.4 Hz, ArH), 7.94 (s, 1H, pyraz-H), 8.11 (d, 1H, J=8.2 Hz, ArH), 8.14 (s, 1H, pyraz-H), 8.18 (d, 1H, J=1.4 Hz, ArH), 8.61 (s, 1H, ArH).

From the more polar fractions was isolated 1-(6-[(1S)-1,2,3,4-tetrahydronaphthalen-1-ylamino]pyrazin-2-yl)-1H-benzimidazole-5-carbonitrile (19 mg)

¹H-n.m.r. (CDCl₃) δ 1.89-2.02 (m, 2H, CH₂), 2.10-2.20 (m, 2H, CH₂), 2.83-2.91 (m, 2H, CH₂), 5.25 (m, 2H, NH+CH), 7.15-7.35 (m, 4H, ArH), 7.62 (dd, 1H, J=8.4, 1.4 Hz, ArH), 7.91-7.95 (m, 2H, ArH+pyraz-H), 8.15 (s, 1H, pyraz-H), 8.52 (br s, 1H, ArH), 8.66 (s, 1H, ArH).

Example 12

1H-Benzimidazole-5-carboxamide

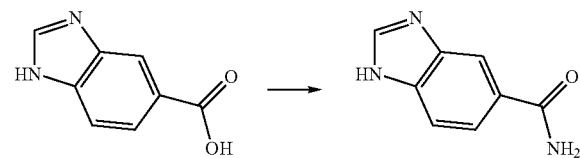

To a stirred suspension of benzimidazole-5-carboxylic acid (5.0 g, 30.8 mmol) in benzene (25 mL) was added thionyl chloride (25 mL) dropwise at room temperature. To this mixture was added DMF (0.1 mL) and it was then heated under reflux for 6 h. Benzene and thionyl chloride was evaporated off under reduced pressure and toluene (20 mL) added to the residue. This was removed under reduced pressure and the acid chloride thus obtained suspended in tetrahydrofuran (20 mL). To this was the added 28% aqueous ammonia (20 mL) drop wise at 0° C., and the resultant mixture was then stirred at room temperature overnight. The precipitate was filtered and washed with cold H₂O to give the primary amide as a brown solid (3.55 g).

¹H-n.m.r. (d₆-DMSO) δ 7.25 (br s, 1H, NH), 7.60 (d, 1H, J=8.4 Hz, ArH), 7.78 (dd, 1H, J=8.4 and 1.6 Hz, ArH), 7.97 (br s, 1H, CONH), 8.18 (br s, 1H, ArH), 8.32 (br s, 1H, ArH).

Example 13

1-(6-{[(1S)-1-Phenylethyl]amino}pyrazin-2-yl)-1H-benzimidazol-5-amine and 1-(6-{[(1S)-1-Phenylethyl]amino}pyrazin-2-yl)-1H-benzimidazol-6-amine

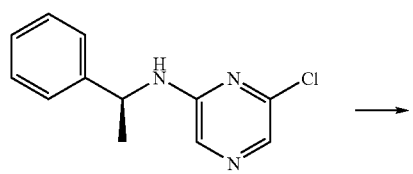

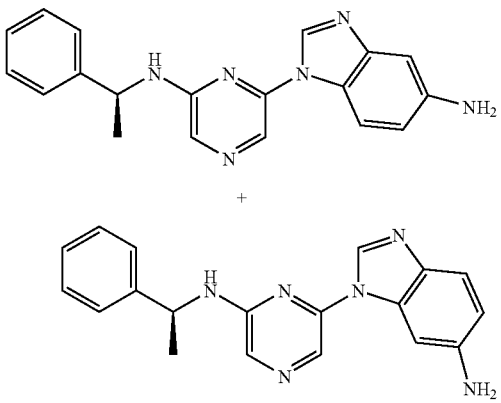

To a stirred solution of 5-amino benzimidazole (290 mg, 2.2 mmol) in anhydrous DMF (10 mL) under N₂ was added caesium carbonate (980 mg) The resulting mixture was stirred at 70° C. for 60 min. To this was added a solution of 6-chloro-N-[(1S)-1-phenylethyl]pyrazin-2-amine (470 mg) in DMF (5 mL) and the resulting mixture was then heated at reflux for 48 h. The DMF was removed under reduced pressure and the residue diluted with chloroform. The organic layer was washed with aqueous Na₂CO₃ dried (Na₂SO₄) and the solvent removed under reduced pressure to furnish the crude product. Column chromatography using dichloromethane-methanol (95:5-92:8) as eluant separated two fractions from unreacted starting material. The higher Rf fraction was assigned as the 6-isomer (276 mg, 42%).

¹H-n.m.r, (CDCl₃) δ 1.64 (d, 3H, J=6.9 Hz, CH₃), 2.90 (br s, 2H, NH₂), 5.05 (m, 1H, CH), 5.21 (d, 1H, NH), 6.70 (dd, 1H, J=8.7, 2.1 Hz, ArH), 6.97 (d, 1H, J=1.8 Hz, ArH), 7.28-7.43 (m, 5H, Ph-H), 7.58 (d, 1H, J=8.4 Hz, ArH), 7.84 (s, 1H, pyraz-H), 8.08 (s, 1H, pyraz-H), 8.21 (s, 1H, ArH). m/z (ES) 331 (M⁺+H).

The lower fraction was assigned as the 5-isomer (170 mg, 26%).

¹H-n.m.r. (CDCl₃) δ 1.64 (d, 3H, J=6.9 Hz, CH₃), 2.85 (br s, 2H, NH₂), 5.01 (m, 1H, CH), 5.19 (d, 1H, NH), 6.70 (dd, 1H, J=8.7, 2.1 Hz, ArH), 7.11 (d, 1H, J=1.8 Hz, ArH), 7.29-7.40 (m, 5H, Ph-H), 7.51 (d, 1H, J=8.7 Hz, ArH), 7.81 (s, 1H, pyraz-H), 8.10 (s, 1H, pyraz-H) 8.32 (s, 1H, ArH).

m/z (ES) 331 (M⁺+H).

Example 14

N-[1-(6-{[(1S)-1-Phenylethyl]amino}pyrazin-2-yl)-1H-benzimidazol-6-yl]-2,2-dimethylpropanamide

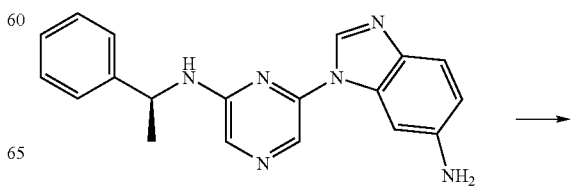

-continued

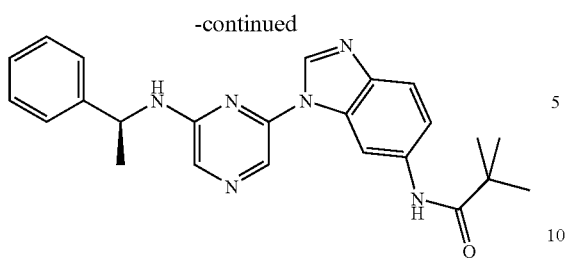

To a stirred solution of 2-(benzylamino)-6-(5-amino-benzimidazo-1-yl)-pyrazine (33 mg, 0.1 mmol) in anhydrous THF (2 mL) under $N_2$ was added triethylamine (38 □l, 0.3 mmol). The solution was cooled at 0° C. and to this was added pivalic acid (12 mg, 0.11 mmol) and EDC (23 mg, 0.12 mmol) and the resulting mixture then stirred at RT. After 64 h the solution was diluted with $H_2O$ and the mixture extracted with $CHCl_3$ (2×15 mL). The combined organic layers were washed with 10% aqueous $Na_2CO_3$, dried $(Na_2SO_4)$ and the solvent removed in vacuo. The residue was purified by column chromatography using dichloromethane-methanol (100:6) as eluant to separate the pure product (15 mg).

$^1$H-n.m.r, $(CDCl_3)$ δ 1.35 (s, 9H, $3CH_3$), 1.65 (d, 3H, J=6.6 Hz, $CH_3$), 5.14 (m, 1H, CH), 5.24 (d, 1H, J=5.7 Hz, NH), 7.13 (d, 1H, J=8.7 Hz, ArH), 7.29-7.47 (m, 5H, ArH), 7.75 (d, 1H, J=8.7 Hz, ArH), 7.81 (s, 1H, pyraz-H), 8.17 (s, 1H, pyraz-H), 8.35 (s, 1H, ArH), 8.69 (s, 1H, CONH).

Example 15

N-[1-(6-{[(1S)-1-Phenylethyl]amino}pyrazin-2-yl)-1H-benzimidazol-5-yl]acetamide

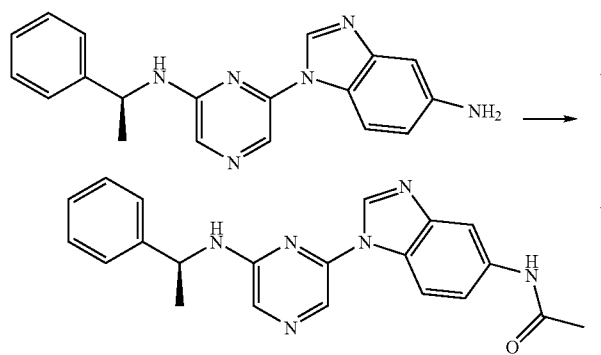

To a stirred solution of 2-(S-α-methylbenzylamino)-6-(5-amino-benzimidazo-1-yl)-pyrazine (66 mg, 0.2 mmol) in anhydrous THF (2 mL) under $N_2$ was added triethylamine (41 mg, 0.4 mmol). The solution was cooled at 0° C. and to this was added acetyl chloride (17 mg, (0.22 mmol) and the resulting mixture then stirred at RT. After 18 h the solution was poured into water (30 mL) and the product extracted into chloroform (2×20 mL). The combined organic layers were dried $(Na_2SO_4)$ and the solvent removed under reduced pressure to furnish the crude product as a pale yellow solid. Column chromatography using dichloromethane-methanol (200:15) as eluant separated the product as a pale yellow solid (38 mg).

$^1$H-n.m.r. $(CDCl_3)$ δ 1.63 (d, 3H, J=6.6 Hz, $CH_3$), 2.21 (s, 3H, $CH_3$), 5.00 (m, 1H, CH), 5.43 (d, 1H, J=5.7 Hz, NH), 7.27-7.38 (m, 5H, ArH), 7.49 (d, 1H, J=9.0 Hz, ArH), 7.61 (d, 1H, J=9.0 Hz, ArH), 7.74 (br s, 1H, CONH), 7.84 (s, 1H, pyraz-H), 7.90 (s, 1H, ArH), 8.11 (s, 1H, pyraz-H), 8.36 (s, 1H, ArH).

Example 16

N-[1-(6-[{(1S)-1-Phenylethyl]amino}pyrazin-2-yl)-1H-benzimidazol-5-yl]methanesulfonamide

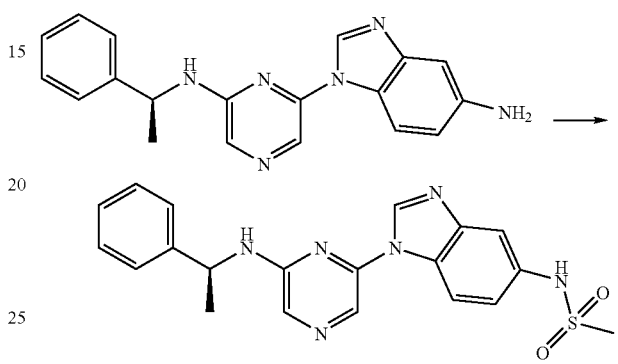

To a stirred solution of 2-(S-α-methylbenzylamino)-6-(5-amino-benzimidazo-1-yl)-pyrazine (33 mg, 0.1 mmol) in anhydrous THF (2 mL) under $N_2$ was added triethylamine (40 mg, 0.4 mmol). The solution was cooled at 0° C. and to this was added methanesulphonyl chloride (25 mg, 0.2 mmol) and the resulting mixture then stirred at RT. After 16 h the solution was poured into water (30 mL) and the product extracted into chloroform (2×15 mL). The combined organic layers were was washed with 10% $Na_2CO_3$, dried $(Na_2SO_4)$ and the solvent removed under reduced pressure to furnish the crude product as a pale yellow solid, Column chromatography, using dichloromethane-methanol (100:6) as eluant, separated the product from the most polar fractions as a pale yellow solid (16 mg).

$^1$H-n.m.r. $(CDCl_3)$ δ 1.65 (d, 3H, J=6.9 Hz, $CH_3$), 3.00 (s, 3H, $CH_3$), 5.02 (m, 1H, CH), 5.27 (d, 1H, J=6.0 Hz, NH), 7.21-7.40 (m, 6H, ArH), 7.64 (d, 1H, J=8.7 Hz, ArH), 7.69 (d, 1H, J=1.9 Hz, ArH), 7.88 (s, 1H, pyraz-H), 8.10 (s, 1H, pyraz-H), 8.41 (s, 1H, ArH).

Example 17

2-(S-α-Methylbenzylamino)-6-(5-(N-methylpiperazin-4-yl-methyl)-benzimidazo-1-yl)-pyrazine

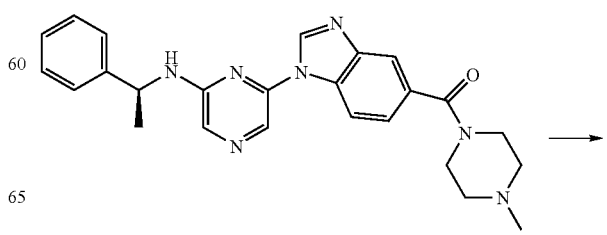

-continued

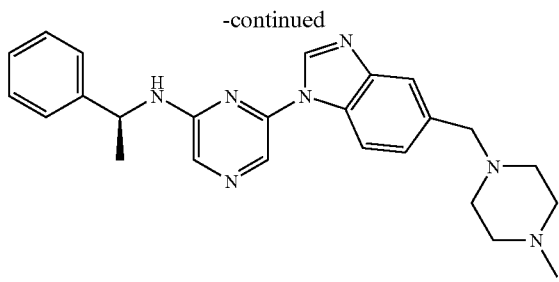

A solution of 3-[6-(S-α-methylbenzylamino)-pyrazin-2-yl]-3H-benzimidazole-5-carboxylic acid N-methylpiperazinylamide (22 mg, (0.05 mmol) in dry THF (1 mL) was added to a suspension of LiAlH$_4$ (4 mg, 0.1 mmol) in THF (1 mL) and the mixture heated at reflux for 4 h. Upon cooling to RT, the solution was treated consecutively with H$_2$O (1 mL), aqueous NaOH (1 mL, 2M) and H$_2$O (5 mL). The resulting mixture was extracted with CHCl$_3$ (2×10 mL) and the combined organic layers dried (Na$_2$SO$_4$). The solvent was removed under reduced pressure and the product purified by flash chromatography using CH$_2$Cl$_2$—MeOH (10:1→1:1) as eluant to afford the product as a yellow solid (11 mg, 52%).

$^1$H-n.m.r. (CDCl$_3$) δ 1.65 (d, 3H, J=6.9 Hz, CH$_3$), 2.58 (s, 3H, NCH$_3$), 2.81 (br s, 4H, CH$_2$), 2.90 (br s, 4H, CH$_2$), 3.74 (s, 2H, NCH$_2$), 5.03 (m, 1H, CH), 5.33 (d, 1H, J=6.0 Hz, NH), 7.25-7.42 (m, 6H, ArH), 7.67 (d, 1H, J=8.4 Hz, ArH), 7.77 (s 1H, ArH), 7.87 (s, 1H, pyraz-H), 8.12 (s, 1H, pyraz-H), 8.39 (s, 1H, ArH).

Example 18

[1-(6-{[1-(4-Fluorophenyl)ethyl]amino}pyrazin-2-yl)-1H-benzimidazol-5-yl]methanol and

[1-(6-{[1-(4-Fluorophenyl)ethyl]amino}pyrazin-2-yl)-1H-benzimidazol-6-yl]methanol

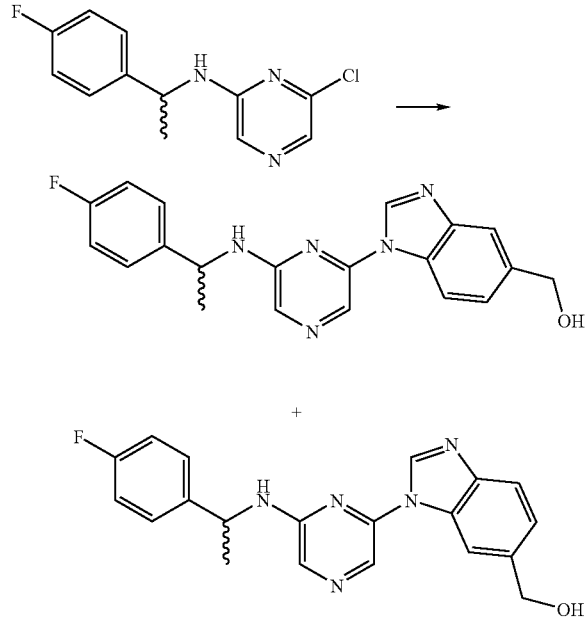

In a procedure analogous to Example 3, reaction of 6-chloro-N-[1-(4-fluorophenyl)ethyl]pyrazin-2-amine (1.80 g, 7.15 mmol) and 5-hydroxymethyl benzimidazole (1.26 g, 8.5 mmol) furnished the two products which were separated by column chromatography using dichloromethane-methanol (98:2-92:8) as eluant. From the less polar fractions was obtained [1-(6-{[1-(4-fluorophenyl)ethyl]amino}pyrazin-2-yl)-1H-benzimidazol-6-yl]methanol as a pale yellow solid (210 mg).

$^1$H-n.m.r. (CDCl$_3$) δ 1.60 (d, 3H, J=6.8 Hz, CH$_3$), 4.93-5.05 (m, 1H, CH), 5.48 (d, 1H, J=6.2 Hz, NH), 6.97-7.07 (m, 2H, ArH), 7.29-739 (m, 3H, ArH), 7.76 (d, 1H, J=9.4 Hz, ArH), 7.79 (s, 1H, pyraz-H), 7.89 (s, 1H, ArH), 8.09 (s, 1H, pyraz-H), 8.34 (s, 1H, ArH).

From the more polar fractions was isolated [1-(6-{[1-(4-fluorophenyl)ethyl]amino}pyrazin-2-yl)-1H-benzimidazol-5-yl]methanol as a yellow solid (265 mg).

$^1$H-n.m.r. (CDCl$_3$) δ 1.62 (d, 3H, J=6.8 Hz, CH$_3$), 4.82 (s, 2H, CH$_2$OH), 4.94-5.06 (m, 1H, CH), 5.29 (d, 1H, J=6.0 Hz, NH), 7.02-7.10 (m, 2H, ArH), 7.29-7.40 (m, 3H, ArH), 7.68 (d, 1H J=8.4 Hz, ArH), 7.80 (d, 1H, J=1.2 Hz, ArH), 7.84 (s, 1H, pyraz-H), 8.12 (s, 1H, pyraz-H), 8.39 (s, 1H, ArH).

Example 19

N-[1-(4-Fluorophenyl)ethyl]-6-{6-[(4-methylpiperazin-1-yl)methyl]-1H-benzimidazol-1-yl}pyrazin-2-amine

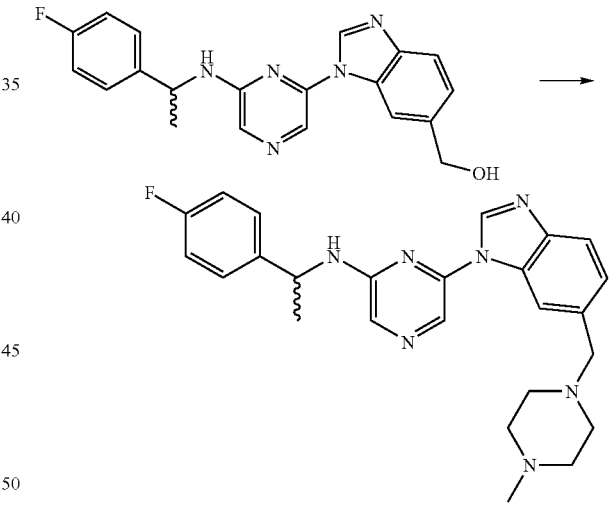

A solution of the alcohol (0.18 g, 0.5 mmol) in dichloromethane (5 mL) was cooled to 0° C. and to this was added diisopropylethylamine (0.13 mL, 0.75 mmol) and methanesulfonyl chloride (46 μL, 0.59 mmol). After stirring at RT for 2 h, a further aliquot of diisopropylethylamine (30 μL) and methanesulfonyl chloride (20 μL) was added. After 1 h. H$_2$O (10 mL) was added and the organic layer collected. The aqueous phase was extracted with dichloromethane (3×5 mL) and the organic layers combined, dried (Na$_2$SO$_4$) and concentrated in vacuo. An aliquot of the crude mesylate thus obtained (100 mg) was dissolved in DMF (2 mL) and to this was added diisopropylethylamine (52 μL, 0.3 mmol) and 1-methylpiperazine (25 μL, 0.45 mmol). The solution was heated at 60° C. overnight. The solution was then concentrated in vacuo and the residue dissolved in dichloromethane (20 mL) and washed with H₂O. The organic layer was dried (Na₂SO₄) and concentrated and the product purified by chromatography using dichloromethane-methanol-aqueous ammonia (95:5:0-95:5:1) to furnish the product as a pale yellow semi-solid (34 mg).

¹H-n.m.r. (CDCl₃) δ 1.63 (d, 3H, J=7.2 Hz, CH₃), 2.26 (s, 3H, NCH₃), 2.45 (br s, 8H, 4×CH₂), 3.62 (s, 2H, CH₂), 4.99-5.11 (m, 1H, CH), 5.41 (d, 1H, J=6.4 Hz, NH), 6.99-7.07 (m, 2H, ArH), 7.30-7.41 (m, 3H, ArH), 7.76 (d, 1H, J=8.4 Hz, ArH), 7.82 (s, 1H, pyraz-H), 7.89 (s, 1H, ArH), 8.17 (s, 1H, pyraz-H), 8.39 (s, 1H, ArH).

Example 20

1-Thien-2-ylethanamine

To a solution of 1-thien-2-ylethanone (505 mg, 4 mmol) and ammonium formate (1.26 g, 20 mmol) in methanol (4 mL) under nitrogen was added dichloro(pentamethylcyclopentadienyl)rhodium (III) dimer (14 mg, 0.023 mmol). The solution was heated at reflux for 7 h. after which time the solution was cooled to room temperature and acidified to pH ~2 with 2M HCl. The mixture was washed with dichloromethane (3×15 mL) and the aqueous phase then basified to pH ~12 by addition of 5M NaOH. The aqueous phase was extracted with dichloromethane (3×15 mL) and the combined organic layers dried (Na₂SO₄) and concentrated to give a pure product (280 mg, 55%).

m/z (EI) 127 (M⁺), 112 (M−15)⁺

Example 21

(1R)-1-(3,4-Difluorophenyl)ethanol

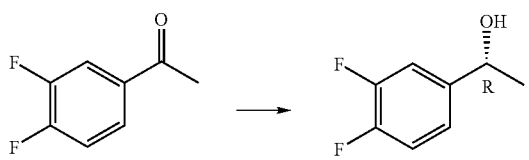

(S,R)-cis-1-amino-2-indanol (284.3 mg, 1.91 mmol, 0.1 eq) was dissolved in tetrahydrofuran (25 mL) in a dry two-necked round-bottomed flask fitted with a dropping funnel and nitrogen inlet. The solution was chilled to approximately 0° C. and N,N-diethylaniline-borane complex (3.50 mL, 19.2 mmol, 1 eq) added dropwise. The mixture was allowed to stir at 0° C. for 30 minutes at which time a solution of 3,4-difluoroacetophenone (2.40 mL) in tetrahydrofuran (40 mL) was added via the dropping funnel over approximately 90 minutes. The solution was allowed to slowly warm to room temperature and stirring continued overnight. Acetone (16 mL) was added to the reaction mixture and the solution allowed to stir for a further hour before being concentrated in vacuo. The residue was treated with toluene (100 mL) and washed with 1 M sulphuric acid (4×50 mL), water (2×50 mL) and brine (50 mL). The organic phase was then dried (Na₂SO₄) and concentrated in vacuo to afford the crude alcohol. Gradient flashmaster chromatography (20 g silica cartridge; 100% petroleum spirits to 100% ethyl acetate) afforded the desired alcohol as a clear oil (2.242 g, 74%).

¹H NMR (CDCl₃ 300 MHz) δ 1.47 (3H, d, J=6.4 Hz), 1.80 (1H, d, J=3.6 Hz), 4.87 (1H, dq, J=3.6, 6.4 Hz), 7.04-7.14 (2H, m), 7.16-7.24 (1H, m).

Example 22

6-Chloro-N-[(1S)-1-(3,4-difluorophenyl)ethyl]pyrazin-2-amine

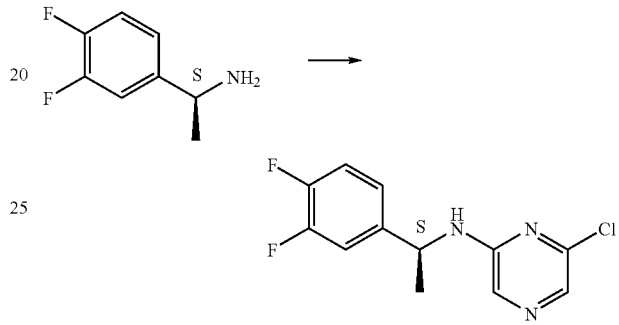

(1S)-1-(3,4-Difluorophenyl)ethanamine (977 mg, 6.2 mmol) and 2,6-dichloropyrazine (1.236 g, 8.3 mmol, 1.3 eq) was dissolved in dioxane (5 mL) and potassium carbonate (1.73 g, 2.0 eq) added to the solution. The mixture was then heated at reflux (110° C.) under a nitrogen atmosphere for 65 hours. The crude reaction mixture was then poured onto cold water (30 mL) and extracted with diethyl ether (3×30 mL). The combined organic extracts were concentrated and subjected to flashmaster chromatography (20 g silica cartridge (8:2 petroleum spirits:ethyl acetate, followed by ethyl acetate flush) to afford the desired pyrazine-adduct as an off-white solid (587 mg, 35%).

¹H NMR (CDCl₃, 300 MHz) 1.56 (3H, d, J=6.9 Hz) 4.88 (1H, dq, J=6.5, 6.9 Hz), 4.97 (1H, brd, J=6.5 Hz), 7.06-7.20 (3H, m), 7.63 (1H, s), 7.82 (1H, s), MS (e.i.) m/z 269 [M'(³⁵Cl), 29%], m/z 271 [M'(³⁷Cl), 10%].

Example 23

1-(6-{[(1S)-1-(3-Fluorophenyl)ethyl]amino}pyrazin-2-yl)-1H-benzimidazole-6-carboxamide

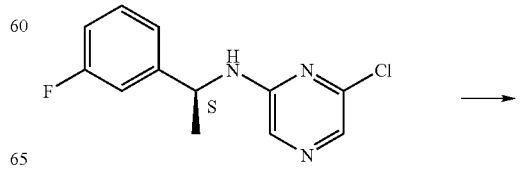

-continued

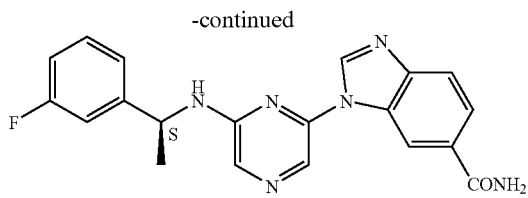

To a stirred mixture of 6-chloro-N-[(1S)-1-(3-fluorophenyl)ethyl]pyrazin-2-amine (242 mg, 0.96 mmol) and 5-benzimidazole carboxamide (318 mg, 1.97 mmol, 2.1 eq) in N,N-dimethylformamide (5 mL) was added cesium carbonate (460 mg, 1.41 mmol, 1.5 eq). This solution was then heated at 120° C. under a nitrogen atmosphere for 48 hours at which time a second amount of cesium carbonate (180 mg, 0.6 eq) was added. The mixture was heated at 120° C. for a further 62 hours before being cooled to room temperature, diluted with chloroform (15 mL) and filtered. The filtrate was then concentrated in vacuo and subjected to silica column chromatography (stepwise gradient from dichloromethane to 9:1 dichloromethane:methanol) to yield the 5-carboxamide product (100.7 mg, 28%) along with the desired 6-carboxamide product (63.7 mg, 18%).

$^1$H NMR (d6-acetone, 300 MHz) δ 1.64 (3H, d, J=6.9 Hz), 2.76-2.80 (2H, brm), 5.35 (1H, m), 6.93 (1H, m), 7.29-7.36 (3H, m), 7.42 (1H, dm, J=7.7 Hz), 7.77 (1H, dd, J=8.5, 0.5 Hz), 7.93 (1H, dd, J=1.7, 8.5 Hz), 8.05 (1H, s), 8.31 (1H, s), 8.73 (1H, s), 8.40 (1H, dd, J=0.5, 1.6 Hz).

MS (e.i.) m/z 376 (M+, 89%).

Other Compounds prepared through methods analogous to those reported above include:

| Example | Compound | Data |
|---|---|---|
| 24 | | [1]H-n.m.r. (CDCl$_3$) δ1.67 (d, 3H, J = 6.9 Hz, CH$_3$), 5.04 (dq, J = 6.9 Hz, 1H, CH), 5.40 (d, 1H, J = 6.9 Hz, NH), 6.92-7.12 (m, 2H, ArH), 7.26-7.38 (m, 1H, ArH), 7.40-7.46 (m, 4H, ArH), 7.61 (dd, 1H, J = 8.4, 1.5 Hz, ArH), 7.89 (d, 1H, J = 8.4 Hz, ArH), 7.91 (s, 1H, pyraz-H), 8.10 (s, 1H, pyraz-H), 8.28 (d, 1H, J = 1.4 Hz, ArH), 8.50 (s, 1H, ArH). |
| 25 | | [1]H-n.m.r. (CDCl$_3$) δ1.66 (d, 3H, J = 6.8 Hz, CH$_3$), 5.02 (m, 1H, CH), 5.26 (d, 1H, J = 5.8 Hz, NH), 7.16-7.25 (m, 3H, ArH), 7.91 (d, 1H, J = 8.4 Hz, ArH), 7.92 (d, J = 0.4 Hz, 1H, pyraz-H), 8.17 (d, 1H, J = 0.4 Hz, pyraz-H), 8.32 (dd, 1H, J = 1.5, 0.7 Hz, ArH), 8.53 (s, 1H, ArH). |
| 26 | | [1]H-n.m.r. (CDCl$_3$) δ1.69 (d, 3H, J = 6.6 Hz, CH$_3$), 5.33 (m, 1H, CH), 5.39 (d, 1H, J = 7.0 Hz, NH), 7.11-7.19 (m, 2H, ArH), 7.26-7.33 (m, 1H, ArH), 7.38 (m, 1H), 7.62 (dd, 1H, J = 8.4, 1.5 Hz, ArH), 7.91 (dd, J = 8.4, 0.6 Hz, 1H), 7.94 (d, 1H, J = 0.3 Hz, pyraz-H), 8.10 (d, 1H, J = 0.3 Hz, ArH), 8.26 (1H, m), 8.52 (s, 1H, ArH). |
| 27 | | [1]H-n.m.r. (CDCl$_3$) δ1.67 (d, 3H, J = 6.6 Hz, CH$_3$), 5.04 (m, 1H, CH), 5.30 (d, 1H, J = 5.9 Hz, NH), 6.99-7.11 (m, 2H, ArH), 7.23 (dm, 1H, J = 7.8 Hz, ArH), 7.41 (ddd, 1H, J = 8.0, 7.9, 5.0 Hz), 7.60 (dd, 1H, J = 8.4, 1.5 Hz, ArH), 7.90 (dd, J = 8.4, 0.7 Hz, 1H), 7.92 (s, 1H, pyraz-H), 8.14 (s, 1H, pyraz-H), 8.25 (d, 1H, J = 1.5, 0.7 Hz), 8.51 (s, 1H, ArH). |

Screening

JAK Tyrosine Kinase Domain Production

JAK kinase domains were produced in the following manner:

JAK1

The kinase domain of human JAK1 was amplified from U937mRNA using the polymerase chain reaction with the following primers:

```
XHOI-J1
5'-CCG CTC GAG ACT GAA GTG GAC CCC ACA CAT-3'

J1-KPNI
5'-CGG GGT ACC TTA TTT TAA AAG TGC TTC AAA-3'
```

JAK1 PCR products were cloned into the pFastBac HTb expression vector (Gibco) via the Xho I and Kpn I sites. The JAK1 plasmid was then transformed into competent DH10Bac cells (Gibco), and the recombinant baculovirus produced prepared for transfection into Sf9 insect cells.

JAK2

The kinase domain of human JAK2 was amplified from U937mRNA using the polymerase chain reaction with the following primers:

```
SALI-jk2
5'-ACG CGT CGA CGG TGC CTT TGA AGA CCG GGA T-3' jk2-NOTI
5'-ATA GTT TAG CGG CCG CTC AGA ATG AAG GTC ATT T-3'
```

JAK2 PCR products were cloned into the pFastBac HTc expression vector (Gibco) via the Sal I and Not I sites. The JAK2 plasmid was then transformed into competent DHL10Bac cells (Gibco), and the recombinant baculovirus produced prepared for transfection into Sf9 insect cells.

JAK3

The kinase domain of human JAK3 was amplified from U937mRNA using the polymerase chain reaction with the following primers:

```
XHOI-J3
5'-CCG CTC GAG TAT GCC TGC CAA GAC CCC ACG-3'

J3-KPNI
5'-CGG GGT ACC CTA TGA AAA GGA CAG GGA GTG-3'
```

JAK3 PCR products were cloned into the pFastBac HTb expression vector (Gibco) via the Xho I and Kpn I sites. The JAK3 plasmid was then transformed into competent DH10Bac cells (Gibco), and the recombinant baculovirus produced prepared for transfection into Sf9 insect cells.

TYK2

The kinase domain of human TYK2 was amplified from A549 mRNA using the polymerase chain reaction with the following primers:

```
HT2EK
5'-GGA GCA CTC GAG ATG GTA GCA CAC AAC CAG GTG-3'

1TY2.2R
5'-GGA GCA GGA ATT CCG GCG CTG CCG GTC AAA TCT GG-3'
```

TYK2 PCR products were cloned into pBlueBacHis2A (Invitrogen) via the EcoRI site. The recombinant TYK2 baculovirus produced was prepared for transfected into Sf9 insect cells.

Large Scale Production of Kinase Domains

Baculovirus preparations from each of the JAK family members were infected into five litres of High Five cells (Invitrogen) grown in High Five serum free medium (Invitrogen) to a cell density of approximately 1-2×10$^6$ cells/ml. Cells are infected with virus at a MOI of 0.8-3.0. Cells were harvested and lysed. JAK kinase domains were purified by affinity chromatography on a Probond (Invitrogen) nickel chelate affinity column.

Assay Protocols

Kinase assays were performed either in a 96 well capture-based ELISA assay or in 384 well Optiplates (Packard) using an Alphascreen Protein Tyrosine Kinase kit. In either case using approximately 15 μg of affinity purified PTK domain in the presence of 50 mM HEPES, pH 7.5, 10 mM MgCl$_2$ 150 mM NaCl and 10 μM-1 mM ATP. The biotinylated substrate biotin-EGPWLEEEEEAYGWMDF-NH$_2$ (final concentration 5 μM) was used as substrate. In the ELISA assay tyrosine phosphorylation was quantitated following transfer to an avidin coated ELISA plate using peroxidase-linked anti-phospho-tyrosine antibody PY20. In the Alphascreen assay, Alphascreen phosphotyrosine acceptor beads followed by streptavidin donor beads were added under subdued light. The ELISA plates were read on a BMG Fluorostar, the Alphascreen plates were read on a Packard Fusion Alpha. Inhibitors were added to the assays fifteen minutes prior to the addition of ATP. Inhibitors were added in aqueous DMSO, with DMSO concentrations never exceeding 1%.

Results

The activity of a range of compounds is shown in Table 3. Compounds that exhibited a capacity to inhibit 50% or greater of enzyme activity at a concentration of 20 μM (measured under standard conditions, see Methods), are designated as "+". Compounds not tested are designated "NT"; while compounds that did not inhibit enzyme activity by 50% at 20 μM are designated "-".

TABLE 3

| CHEMISTRY | Jak2 | Jak3 | zap70 | tie2 | hck | abl | fms | kdr | btk |
|---|---|---|---|---|---|---|---|---|---|
| C25H22N6O2S | + | + | NT | NT | NT | NT | NT | NT | NT |
| C28H33N7O2 | + | + | + | NT | NT | NT | NT | + | NT |
| C19H16ClN5 | − | − | NT | NT | NT | NT | NT | NT | NT |
| C22H19N7 | − | − | NT | NT | NT | NT | NT | NT | NT |
| C20H19N5 | + | − | + | NT | NT | + | NT | NT | NT |
| C18H16N6 | − | − | NT | NT | NT | NT | NT | + | NT |

TABLE 3-continued

| CHEMISTRY | Jak2 | Jak3 | zap70 | tie2 | hck | abl | fms | kdr | btk |
|---|---|---|---|---|---|---|---|---|---|
| C25H28N8O | + | − | + | NT | + | + | NT | + | NT |
| C32H34N8O | − | − | + | NT | + | NT | NT | NT | NT |
| C16H11N5 | + | − | NT | NT | NT | NT | NT | NT | NT |
| C16H11N5 | + | − | NT | NT | NT | NT | NT | NT | NT |
| C18H14N4O2 | − | − | NT | NT | NT | + | NT | NT | NT |
| C17H13N5 | + | − | + | NT | NT | NT | NT | NT | NT |

TABLE 3-continued
| CHEMISTRY | Jak2 | Jak3 | zap70 | tie2 | hck | abl | fms | kdr | btk |
|---|---|---|---|---|---|---|---|---|---|
| 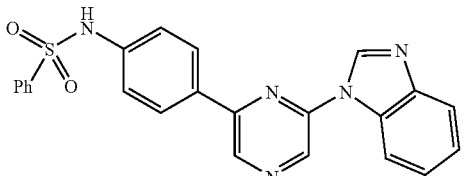 C23H17N5O2S | + | + | NT | NT | NT | NT | NT | NT | NT |
| 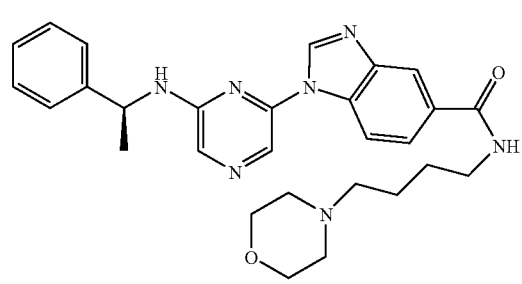 C28H33N7O2 | + | − | + | NT | NT | + | NT | NT | NT |
| 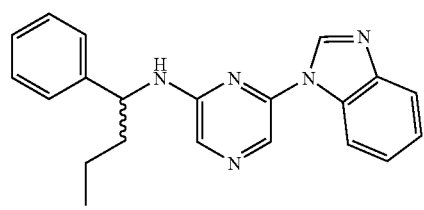 C21H21N5 | + | − | NT | NT | NT | NT | NT | NT | NT |
| 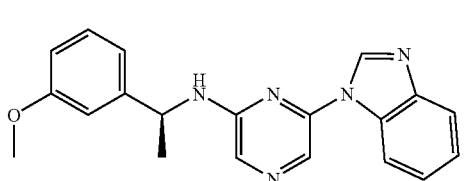 C20H19N5O | − | − | NT | NT | NT | NT | NT | + | NT |
| 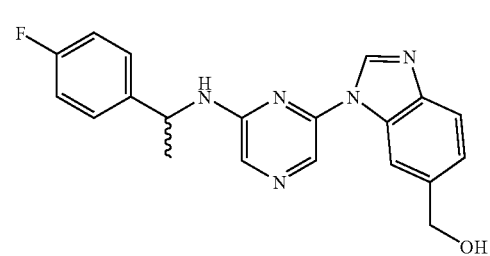 C20H18FN5O | + | − | NT | NT | NT | NT | NT | + | NT |
| 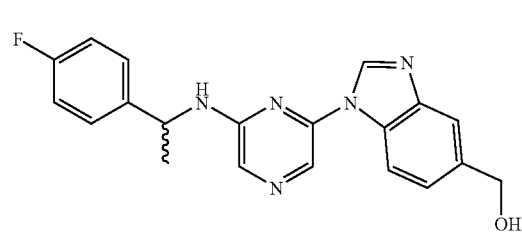 C20H18FN5O | − | − | NT | NT | NT | NT | NT | + | NT |

TABLE 3-continued

| CHEMISTRY | Jak2 | Jak3 | zap70 | tie2 | hck | abl | fms | kdr | btk |
|---|---|---|---|---|---|---|---|---|---|
| C25H28FN7 | − | − | NT | NT | NT | NT | NT | NT | NT |
| C24H27FN6 | − | − | NT | NT | NT | NT | NT | NT | NT |
| C24H28FN7 | − | − | NT | NT | NT | NT | NT | + | NT |
| C25H29FN7 | − | − | NT | NT | NT | NT | NT | + | NT |
| C24H27FN6 | − | − | NT | NT | NT | NT | NT | + | NT |

TABLE 3-continued

| CHEMISTRY | Jak2 | Jak3 | zap70 | tie2 | hck | abl | fms | kdr | btk |
|---|---|---|---|---|---|---|---|---|---|
| C22H23FN6 | − | − | NT | NT | NT | NT | NT | + | NT |
| C24H28FN7 | − | − | NT | NT | NT | NT | NT | NT | NT |
| C18H15FN6 | − | − | NT | NT | NT | NT | NT | NT | NT |
| C18H15FN6 | + | − | NT | NT | NT | NT | NT | + | NT |
| C20H18FN5O | + | − | NT | NT | + | NT | NT | NT | + |
| C20H18FN5O | − | − | NT | NT | NT | NT | NT | NT | NT |

TABLE 3-continued

| CHEMISTRY | Jak2 | Jak3 | zap70 | tie2 | hck | abl | fms | kdr | btk |
|---|---|---|---|---|---|---|---|---|---|
| C24H26FN7 | − | + | NT | + | NT | NT | NT | NT | NT |
| C24H25FN6O | + | − | NT | NT | + | NT | NT | NT | NT |
| C25H27FN6 | + | + | NT | NT | NT | NT | NT | NT | NT |
| C25H27FN6O | + | − | NT | NT | NT | NT | NT | NT | NT |
| C24H25FN6 | + | − | NT | + | NT | NT | NT | NT | NT |

TABLE 3-continued
| CHEMISTRY | Jak2 | Jak3 | zap70 | tie2 | hck | abl | fms | kdr | btk |
|---|---|---|---|---|---|---|---|---|---|
| 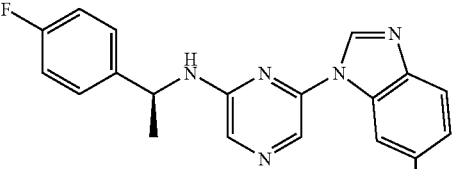<br>C26H31FN8 | − | − | NT | NT | NT | NT | NT | NT | NT |
| 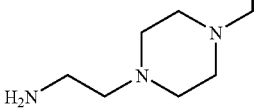<br>C24H27FN6O2 | + | − | NT | NT | + | NT | NT | NT | NT |
| 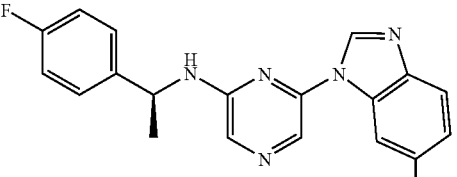<br>C21H16N6 | + | + | NT | + | NT | NT | NT | NT | NT |
| 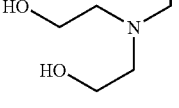<br>C21H16N6 | + | + | NT | + | NT | NT | NT | + | NT |
| 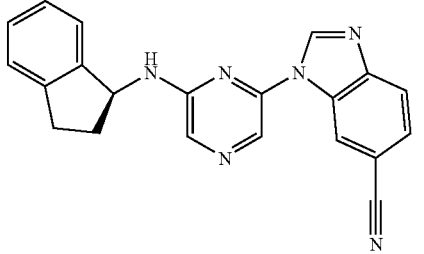<br>C24H18N6 | − | − | NT | NT | NT | NT | NT | NT | NT |

TABLE 3-continued

| CHEMISTRY | Jak2 | Jak3 | zap70 | tie2 | hck | abl | fms | kdr | btk |
|---|---|---|---|---|---|---|---|---|---|
| C24H18N6 | − | − | NT | NT | NT | NT | + | NT | NT |
| C20H16FN9 | + | − | NT | NT | NT | NT | NT | NT | NT |
| C20H16FN9 | − | − | + | NT | NT | NT | NT | NT | NT |
| C18H16FN5 | + | + | + | NT | NT | NT | NT | NT | NT |
| C20H18N6 | + | + | NT | NT | NT | NT | NT | NT | NT |
| C20H16N6 | + | + | NT | NT | NT | NT | NT | NT | NT |

TABLE 3-continued
| CHEMISTRY | Jak2 | Jak3 | zap70 | tie2 | hck | abl | fms | kdr | btk |
|---|---|---|---|---|---|---|---|---|---|
| 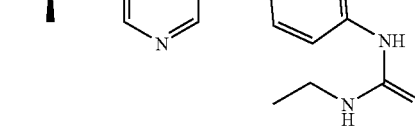<br>C22H23N7O | + | − | NT | NT | NT | NT | + | NT | NT |
| 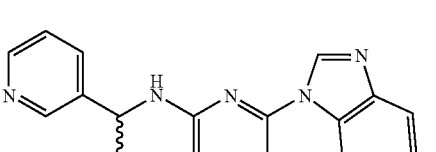<br>C19H15N7 | − | − | NT | NT | NT | + | NT | NT | NT |
| <br>C19H15N7 | + | + | NT | NT | + | NT | NT | NT | NT |
| 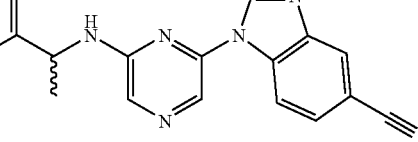<br>C19H16FN5 | − | − | NT | NT | NT | NT | NT | NT | NT |
| 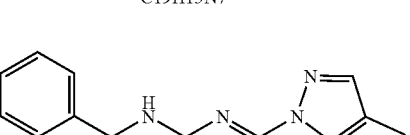<br>C19H16FN5 | − | − | NT | NT | NT | NT | NT | NT | NT |
| 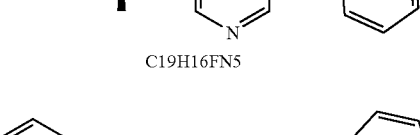<br>C20H14F2N6 | + | + | NT | NT | NT | NT | NT | NT | NT |

TABLE 3-continued

| CHEMISTRY | Jak2 | Jak3 | zap70 | tie2 | hck | abl | fms | kdr | btk |
|---|---|---|---|---|---|---|---|---|---|
| C20H14F2N6 | + | + | NT | NT | NT | NT | NT | NT | NT |
| C20H15FN6 | + | + | NT | NT | + | NT | NT | NT | NT |
| C20H15FN6 | + | + | NT | NT | NT | NT | NT | NT | NT |
| C22H18N6 | − | − | NT | NT | NT | NT | NT | NT | NT |
| C22H18N6 | + | + | NT | NT | NT | NT | + | NT | NT |
| C20H15FN6 | + | + | NT | NT | NT | NT | + | NT | NT |

TABLE 3-continued
| CHEMISTRY | Jak2 | Jak3 | zap70 | tie2 | hck | abl | fms | kdr | btk |
|---|---|---|---|---|---|---|---|---|---|
| 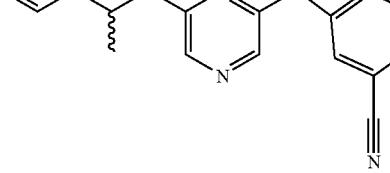<br>C20H14F2N6 | + | + | NT | NT | + | NT | NT | NT | NT |
| 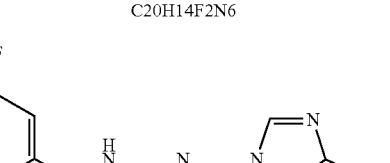<br>C20H14F2N6 | + | − | NT | NT | NT | NT | NT | NT | NT |
| 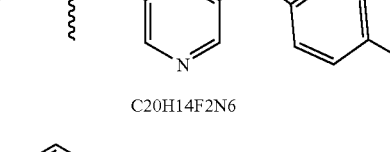<br>C21H15F3N6 | + | − | NT | NT | NT | NT | NT | NT | NT |
| 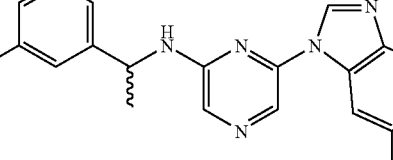<br>C21H15F3N6 | − | − | NT | NT | NT | NT | NT | NT | NT |
| 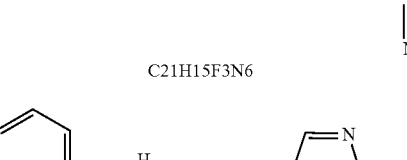<br>C20H14ClFN6 | + | + | NT | NT | NT | NT | NT | NT | NT |
| 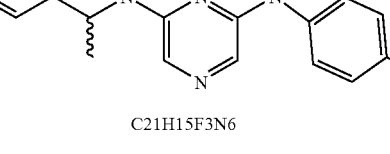<br>C20H14ClFN6 | + | − | NT | NT | + | NT | NT | NT | NT |

TABLE 3-continued

| CHEMISTRY | Jak2 | Jak3 | zap70 | tie2 | hck | abl | fms | kdr | btk |
|---|---|---|---|---|---|---|---|---|---|
| C21H15F3N6O | − | − | NT | NT | NT | NT | NT | NT | NT |
| C21H15F3N6O | − | − | NT | NT | NT | NT | NT | NT | NT |
| C21H16N6 | − | − | NT | NT | NT | NT | NT | NT | NT |
| C21H16N6 | − | − | NT | NT | NT | NT | NT | NT | NT |
| C21H16N6 | − | − | NT | NT | NT | NT | NT | NT | NT |
| C21H16N6 | − | − | NT | NT | NT | NT | NT | NT | NT |

TABLE 3-continued

| CHEMISTRY | Jak2 | Jak3 | zap70 | tie2 | hck | abl | fms | kdr | btk |
|---|---|---|---|---|---|---|---|---|---|
| C21H18N6 | + | + | NT | NT | NT | NT | NT | NT | NT |
| C21H18N6 | + | + | NT | + | NT | NT | NT | + | NT |
| C18H16N6 | − | − | NT | NT | NT | NT | NT | NT | NT |
| C18H16N6 | − | − | NT | NT | NT | NT | NT | NT | NT |
| C18H15FN6 | − | − | NT | NT | NT | NT | NT | NT | NT |
| C18H15FN6 | − | − | NT | NT | NT | NT | NT | NT | NT |
| C21H18N6 | + | + | + | NT | NT | NT | NT | NT | NT |

TABLE 3-continued

| CHEMISTRY | Jak2 | Jak3 | zap70 | tie2 | hck | abl | fms | kdr | btk |
|---|---|---|---|---|---|---|---|---|---|
| C21H18N6 | + | − | NT | NT | NT | NT | NT | NT | NT |
| C21H18N6 | + | + | NT | NT | NT | NT | NT | + | NT |
| C21H18N6 | − | − | NT | NT | NT | NT | NT | NT | NT |
| C21H18N6 | + | + | NT | NT | NT | NT | NT | + | NT |
| C21H18N6 | + | + | NT | NT | NT | NT | NT | NT | NT |
| C12H6ClN5 | − | − | NT | NT | NT | NT | NT | NT | NT |

TABLE 3-continued

| CHEMISTRY | Jak2 | Jak3 | zap70 | tie2 | hck | abl | fms | kdr | btk |
|---|---|---|---|---|---|---|---|---|---|
| C22H18N6 | − | − | NT | NT | NT | NT | NT | NT | NT |
| C22H18N6 | + | + | NT | NT | NT | NT | + | NT | NT |
| C22H18N6O | − | + | NT | NT | NT | NT | NT | NT | NT |
| C22H18N6O | − | − | NT | NT | NT | NT | NT | NT | NT |
| C22H18N6O | − | − | NT | NT | + | NT | NT | NT | NT |
| C22H18N6O | − | − | NT | NT | NT | NT | NT | NT | NT |
| C22H18N6O | − | − | NT | NT | NT | NT | NT | NT | NT |

TABLE 3-continued

| CHEMISTRY | Jak2 | Jak3 | zap70 | tie2 | hck | abl | fms | kdr | btk |
|---|---|---|---|---|---|---|---|---|---|
| C21H15FN6 | − | − | NT | NT | NT | NT | NT | NT | NT |
| C21H15FN6 | + | + | NT | + | NT | NT | NT | NT | NT |
| C21H15BrN6 | − | + | NT | NT | NT | NT | NT | NT | NT |
| C21H15BrN6 | − | − | NT | NT | NT | NT | NT | NT | NT |
| C21H17FN6 | + | + | NT | + | NT | NT | NT | NT | NT |
| C19H15N7 | + | + | NT | NT | NT | NT | NT | NT | NT |

TABLE 3-continued

| CHEMISTRY | Jak2 | Jak3 | zap70 | tie2 | hck | abl | fms | kdr | btk |
|---|---|---|---|---|---|---|---|---|---|
| 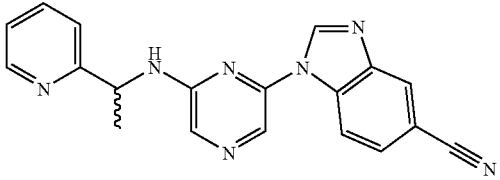 C19H15N7 | + | – | NT | NT | NT | NT | NT | NT | NT |

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

1. Kozma S C, Redmond S M, Fu X C, Saurer S M, Groner B, and Hynes N E. (1988) Activation of the receptor kinase domain of the trk oncogene by recombination with two different cellular sequences. *EMBO J.* 7, 147-54
2. Spiotto M T, and Chung T D. (2000) STAT3 mediates IL6-induced growth inhibition in the human prostate cancer cell line LNCaP. *Prostate* 42, 88-98
3. Wilks A F, Harpur A G, Kurban R R, Ralph S J, Zurcher G, Ziemiecki A. (1991) Two novel protein-tyrosine kinases, each with a second phosphotransferase-related catalytic domain, define a new class of protein kinase. *Mol Cell Biol.* 11, 2057-65
4. Wilks A F, and Kurban R R (1988) Isolation and structural analysis of murine c-fes cDNA clones. *Oncogene* 3, 289-94
5. Sadowski I, Stone J C, Pawson T. (1986) A noncatalytic domain conserved among cytoplasmic protein-tyrosine kinases modifies the kinase function and transforming activity of Fujinami sarcoma virus P130gag-fps. *Mol Cell Biol.* 6, 4396-408

The invention claimed is:
1. A compound of formula (I)

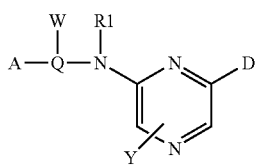

wherein:
D is a heterocyclic ring selected from:

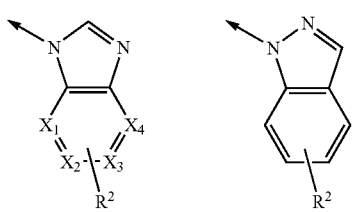

where $X_1$, $X_2$, $X_3$, $X_4$ are optionally substituted carbon, or one of $X_1$, $X_2$, $X_3$, $X_4$ is nitrogen and the rest optionally substituted carbon;

$R^2$ is 0-3 substituents independently selected from the group consisting of halogen, $C_{1-4}$ alkyl, $CF_3$, $OCF_3$, $OCHF_2$, CN, aryl, hetaryl, $C_{1-4}$ alkylOH, $C_{1-4}$ alkylNR$^3$R$^4$, $C_{1-4}$alkylhetaryl, $OC_{1-4}$ alkyl, $OC_{1-4}$ alkylNR$^3$R$^4$, $OC_{1-4}$alkylhetaryl, $OC_{1-4}$ alkylOH, $CO_2R^3$, CONR$^3$R$^4$, NR$^3$R$^4$, nitro, NR$^3$COR$^4$, NR$^5$CONR$^3$R$^4$, NR$^3$SO$_2$R$^4$, $C_{1-4}$alkylNR$^3$COR$^4$, $C_{1-4}$alkylNR$^5$CONR$^3$R$^4$ and $C_{1-4}$alkylNR$^3$SO$_2$R$^4$;

$R^3$ and $R^4$ are each independently H, $C_{1-4}$ alkyl, $C_{1-4}$alkyl OH, $C_{1-4}$alkylNR$^{19}$R$^{20}$, $C_{1-4}$ alkyl cycloalkyl, $C_{3-8}$ cyclohetalkyl, aryl, $C_{1-4}$ alkylaryl, hetaryl, or $C_{1-4}$ alkylhetaryl, or may be joined to form an optionally substituted 3-8 membered (saturated or unsaturated) ring optionally containing an atom selected from O, S and NR$^6$;

and R$^5$ is H, $C_{1-4}$ alkyl, aryl or hetaryl;

R$^6$ is selected from the group consisting of H, $C_{1-4}$ alkyl, $C_{1-4}$alkylNR$^{19}$R$^{20}$, aryl, hetaryl, $C_{1-4}$ alkyl aryl and $C_{1-4}$ alkyl hetaryl;

R$^{19}$ and R$^{20}$ are each independently H or $C_{1-4}$alkyl;

R$^1$ is H, $C_{1-4}$ alkyl, $C_{3-6}$ cycloalkyl, or may form a 5-8 membered ring onto the ortho position of ring A;

A is aryl or hetaryl optionally substituted with 0-3 substituents independently selected from the group consisting of halogen, $C_{1-4}$ alkyl, $CF_3$, $OCF_3$, CN, NR$^8$R$^9$, aryl, hetaryl, $C_{1-4}$ alkylNR$^8$R$^9$, $OC_{1-4}$ alkylNR$^8$R$^9$, nitro, NR$^{10}$C$_{1-4}$NR$^8$R$^9$, NR$^8$COR$^9$, NR$^{10}$CONR$^8$R$^9$, NR$^8$SO$_2$R$^9$, CONR$^8$R$^9$ and CO$_2$R$^8$;

R$^8$ and R$^9$ are each independently H, $C_{1-4}$ alkyl, aryl or together form an optionally substituted 4-8 membered ring which may contain a heteroatom selected from O, S and NR$^{11}$;

R$^{10}$ is H or $C_{1-4}$ alkyl;

R$^{11}$ is H or $C_{1-4}$ alkyl; and either Q is $C_{1-4}$ alkylene; and W is H, $C_{1-4}$alkyl, or $C_{2-6}$alkenyl or may form a 5-8 membered ring onto the ortho position of ring A; where $C_{1-4}$alkyl or $C_{2-6}$alkenyl may be optionally substituted with $C_{1-4}$alkyl, OH, $OC_{1-4}$ alkyl or NR$^{12}$R$^{13}$; R$^{12}$ and R$^{13}$ are each independently H, $C_{1-4}$alkyl, or may be joined to form an optionally substituted 3-8 membered ring optionally containing an atom selected from O, S and NR$^{14}$; R$^{14}$ is H or $C_{1-4}$ alkyl; or Q and W are absent;

Y is 0-2 substituents selected from H, $C_{1-4}$ alkyl, NR$^{15}$R$^{16}$;

$R^{15}$ and $R^{16}$ are independently H or $C_{1-4}$alkyl; and pharmaceutically acceptable salts or diastereomers thereof;
or
a compound selected from a group consisting of:

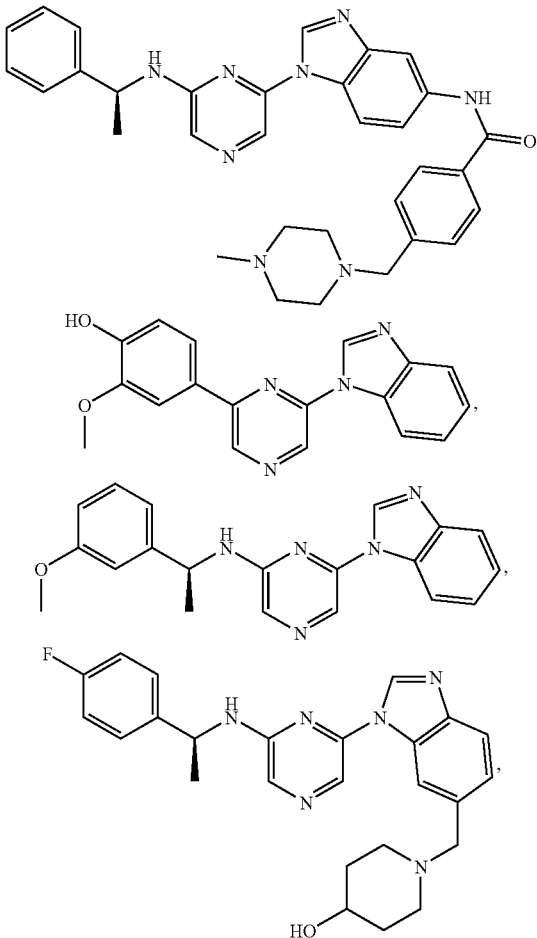

and pharmaceutically acceptable salts, or diastereomers thereof; or
a compound selected from:

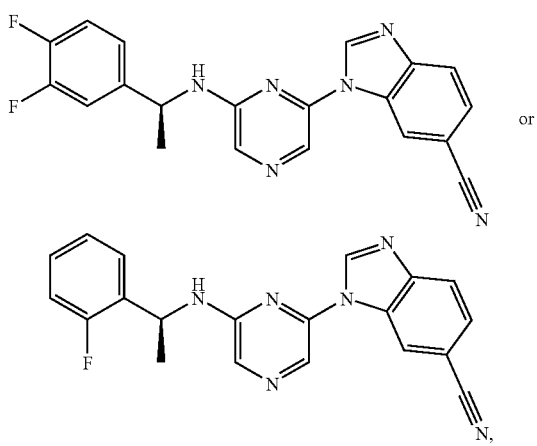

or a pharmaceutically acceptable salt, or diastereomer thereof.

2. A compound according to formula (I) of claim 1, wherein the compound is of formula (II):

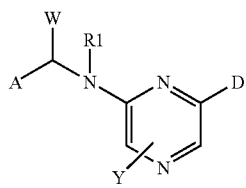

wherein:
D is a heterocyclic ring of the formula:

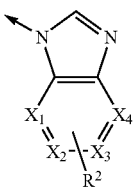

where $X_1$, $X_2$, $X_3$, $X_4$ are optionally substituted carbon, or one of $X_1$, $X_2$, $X_3$, $X_4$ is N and the rest optionally substituted carbon;

$R^2$ is 0-3 substituents independently selected from the group consisting of halogen, $C_{1-4}$ alkyl, $CF_3$, $OCF_3$, $OCHF_2$, CN, aryl, hetaryl, $C_{1-4}$ alkylOH, $C_{1-4}$alkylNR$^3$R$^4$, $C_{1-4}$alkylhetaryl, $OC_{1-4}$ alkyl, $OC_{1-4}$ alkylNR$^3$R$^4$, $OC_{1-4}$alkylhetaryl, $OC_{1-4}$ alkylOH, $CO_2R^3$, $CONR^3R^4$, $NR^3R^4$, nitro, $NR^3COR^4$, $NR^5CONR^3R^4$, $NR^3SO_2R^4$, $C_{1-4}$alkylNR$^3$COR$^4$, $C_{1-4}$alkylNR$^5$CONR$^3$R$^4$ and $C_{1-4}$alkylNR$^3$SO$_2$R$^4$;

$R^3$ and $R^4$ are each independently H, $C_{1-4}$ alkyl, $C_{1-4}$alkyl OH, $C_{1-4}$alkylNR$^{19}$R$^{20}$, $C_{1-4}$ alkyl cycloalkyl, $C_{3-8}$ cyclohetalkyl, aryl, $C_{1-4}$ alkylaryl, hetaryl, or $C_{1-4}$ alkylhetaryl, or may be joined to form an optionally substituted 3-8 membered (saturated or unsaturated) ring optionally containing an atom selected from O, S and $NR^6$;

and $R^5$ is H, $C_{1-4}$ alkyl, aryl or hetaryl;

$R^6$ is selected from the group consisting of H, $C_{1-4}$ alkyl, $C_{1-4}$alkylNR$^{19}$R$^{20}$, aryl, hetaryl, $C_{1-4}$ alkyl aryl, and $C_{1-4}$ alkyl hetaryl;

$R^{19}$ and $R^{20}$ are each independently H or $C_{1-4}$alkyl;

$R^1$ is H, $C_{1-4}$ alkyl, $C_{3-6}$ cycloalkyl, or may form a 5-8 membered ring onto the ortho position of ring A;

A is aryl, or hetaryl optionally substituted with 0-3 substituents independently selected from the group consisting of halogen, $C_{1-4}$ alkyl, $CF_3$, $OCF_3$, CN, $NR^8R^9$, aryl, hetaryl, $C_{1-4}$ alkylNR$^8$R$^9$, $OC_{1-4}$ alkylNR$^8$R$^9$, nitro, $NR^{10}C_{1-4}NR^8R^9$, $NR^8COR^9$, $NR^{10}CONR^8R^9$, $NR^8SO_2R^9$, $CONR^8R^9$ and $CO_2R^8$;

$R^8$ and $R^9$ are each independently H, $C_{1-4}$ alkyl, aryl or together form an optionally substituted 4-8 membered ring which may contain a heteroatom selected from O, S and $NR^{11}$;

$R^{10}$ is H or $C_{1-4}$ alkyl;

$R^{11}$ is H or $C_{1-4}$ alkyl;

W is selected from the group consisting of H, $C_{1-4}$alkyl, and $C_{2-6}$alkenyl or may form a 5-8 membered ring onto the ortho position of ring A; where $C_{1-4}$alkyl or $C_{2-6}$alkenyl may be optionally substituted with $C_{1-4}$alkyl, OH, $OC_{1-4}$alkyl and $NR^{12}R^{13}$;

$R^{12}$ and $R^{13}$ are each independently H, $C_{1-4}$alkyl, or may be joined to form an optionally substituted 3-8 membered ring optionally containing an atom selected from O, S and $NR^{14}$;

$R^{14}$ is H or $C_{1-4}$ alkyl;

Y is 0-2 substituents selected from the group consisting of H, $C_{1-4}$ alkyl and $NR^{15}R^{16}$;

$R^{15}$ and $R^{16}$ are independently H or $C_{1-4}$alkyl; or a pharmaceutically acceptable salt, or diastereomer thereof.

3. A compound selected from the group consisting of:

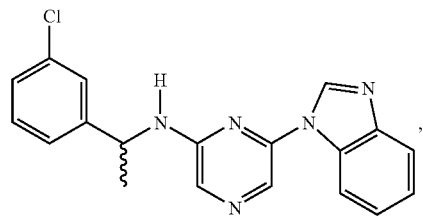,

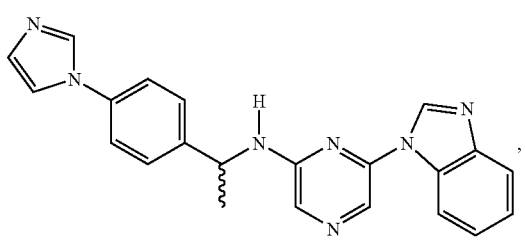,

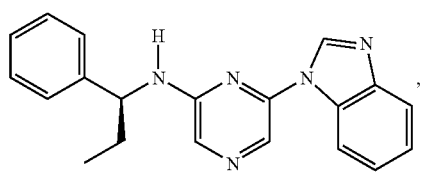,

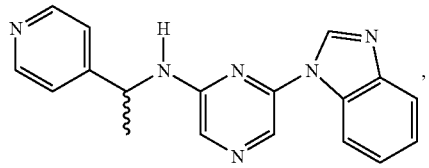,

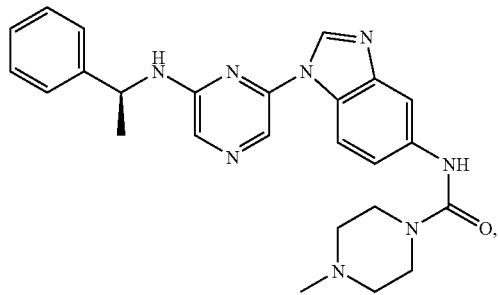,

-continued

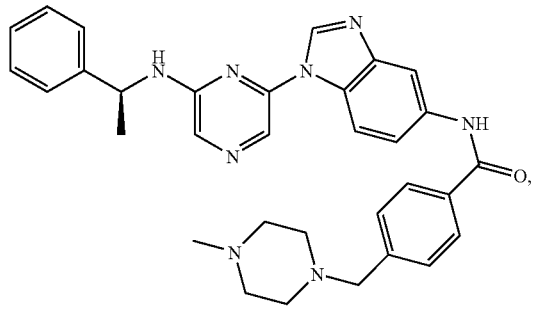,

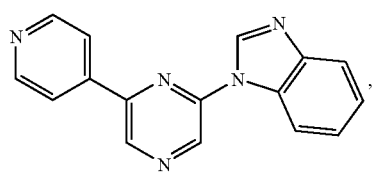,

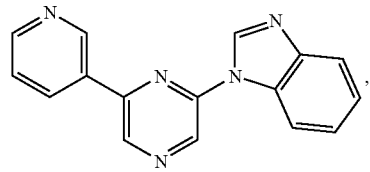,

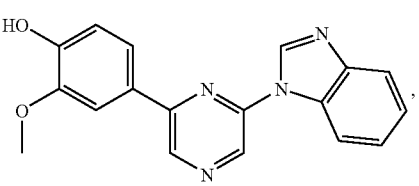,

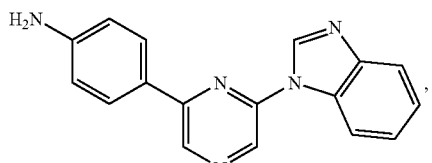,

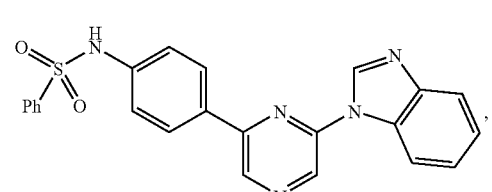,

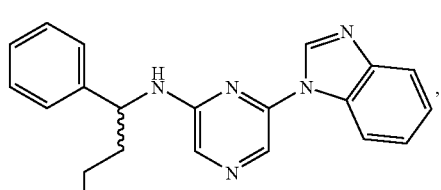,

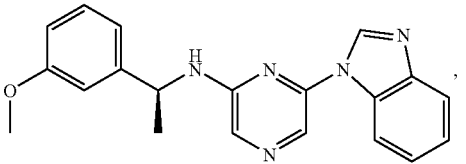,

75
-continued
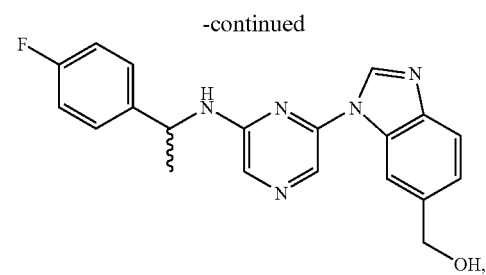
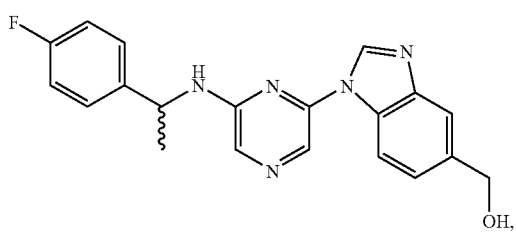
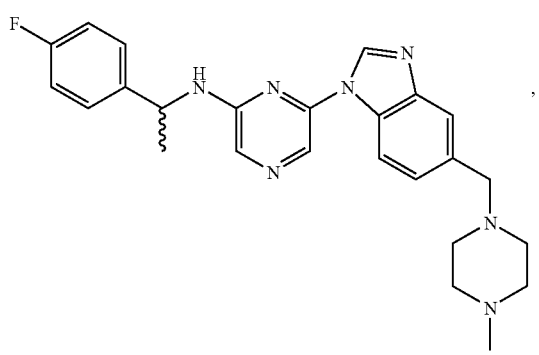
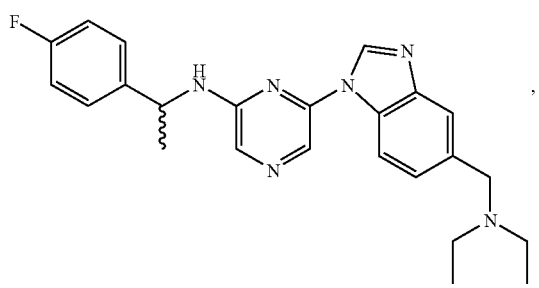
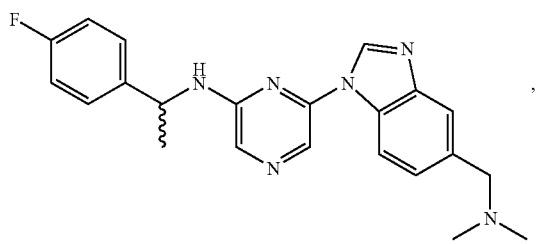
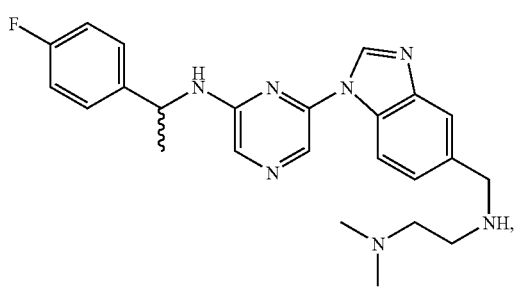
76
-continued
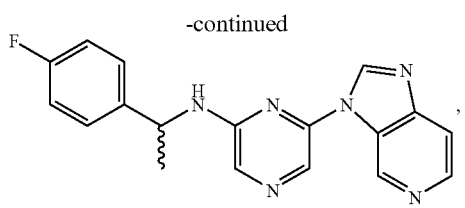
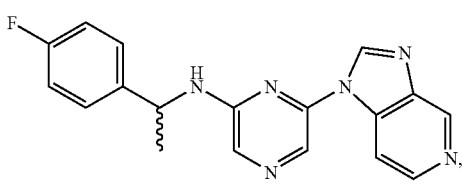
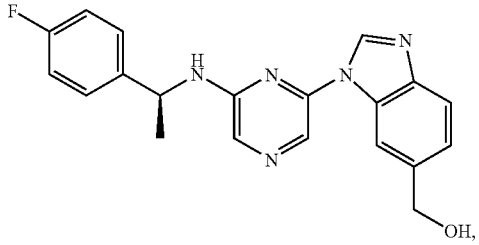
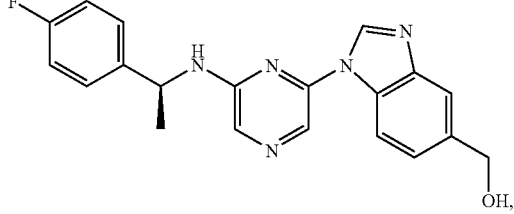
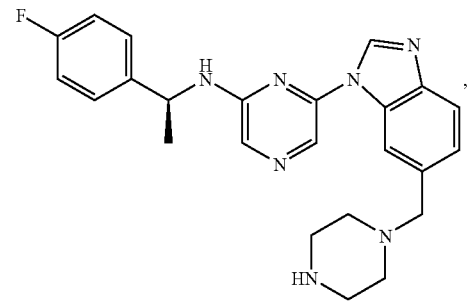
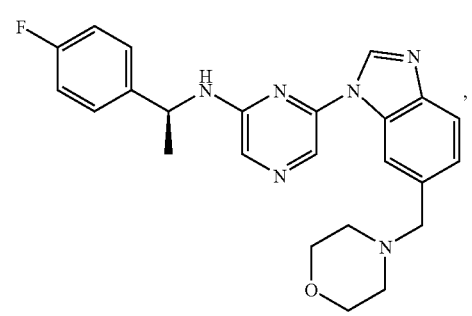

-continued
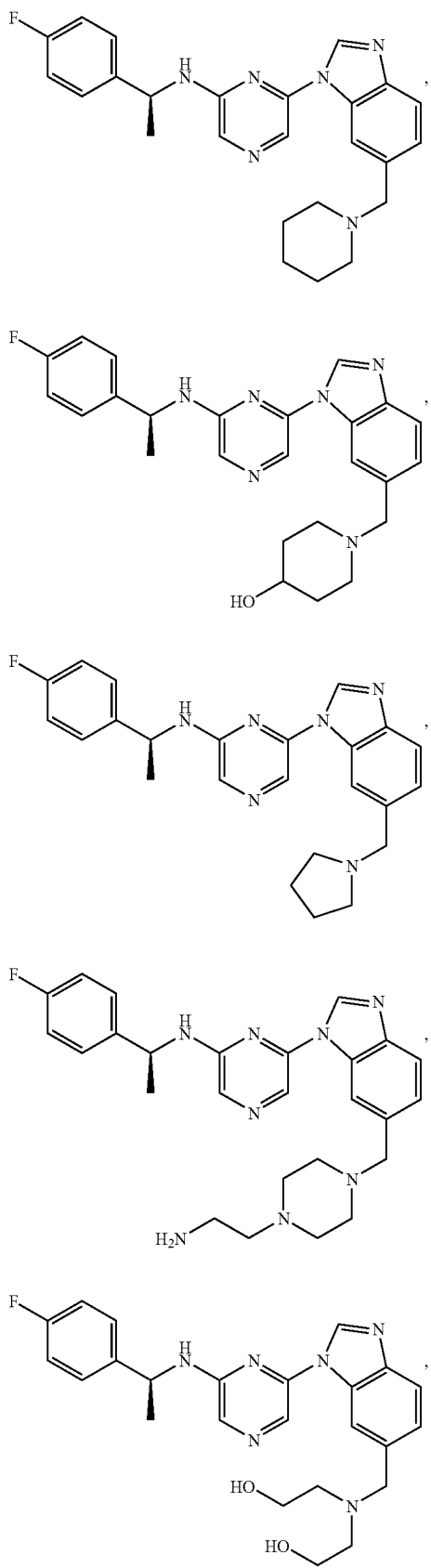
-continued
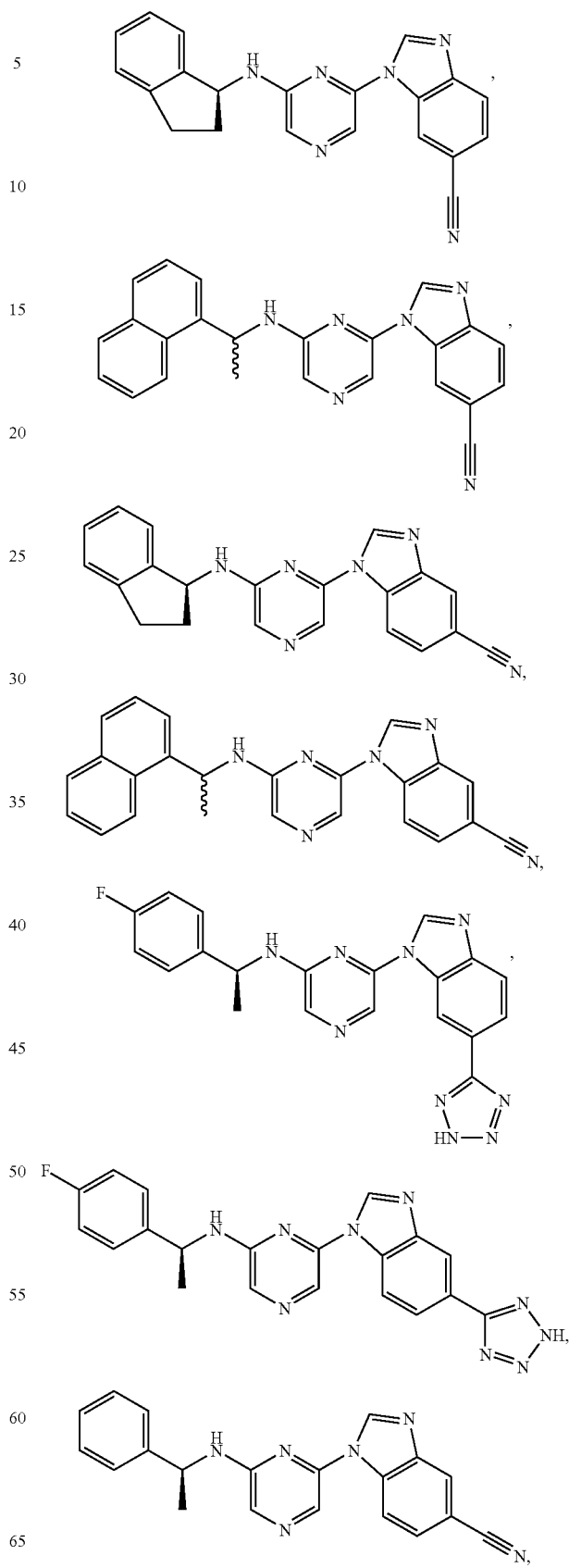

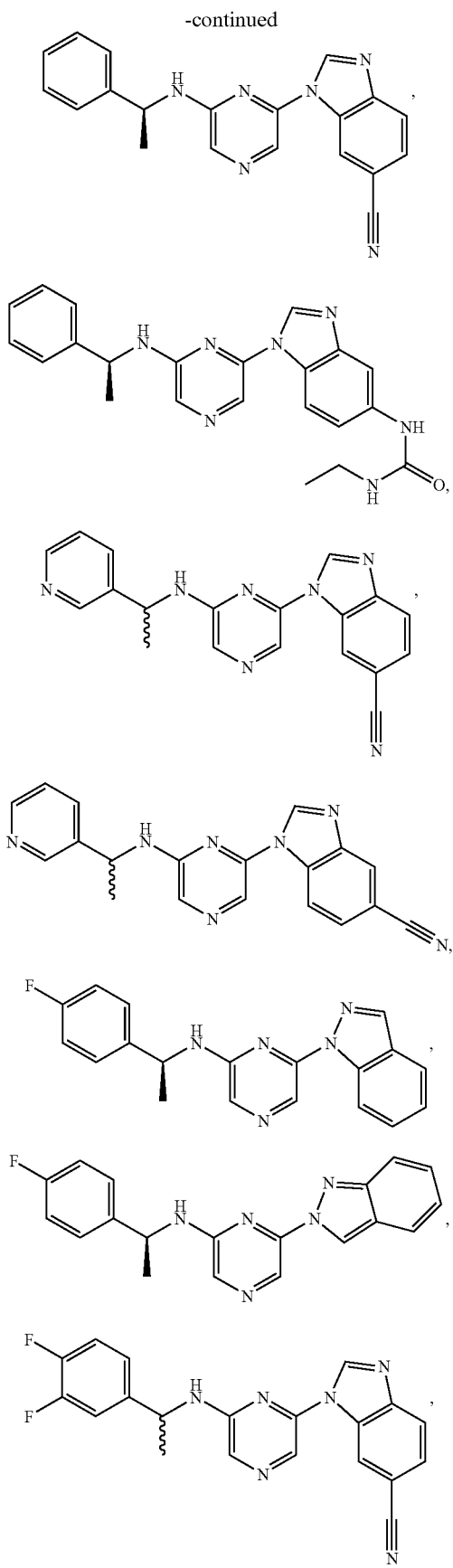

-continued
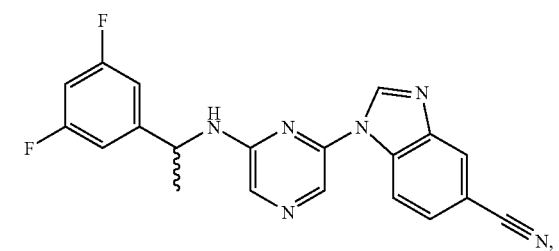
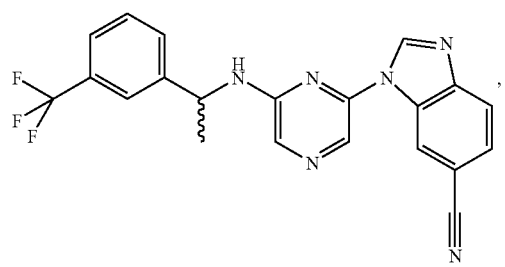
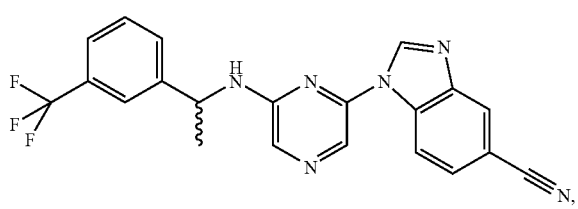
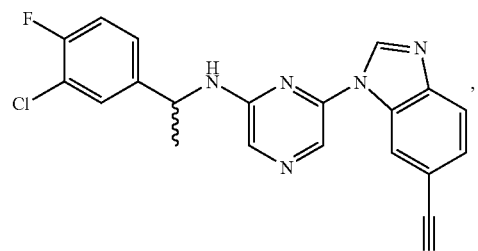
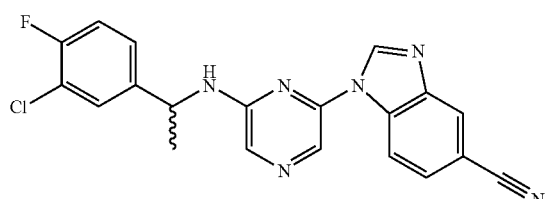
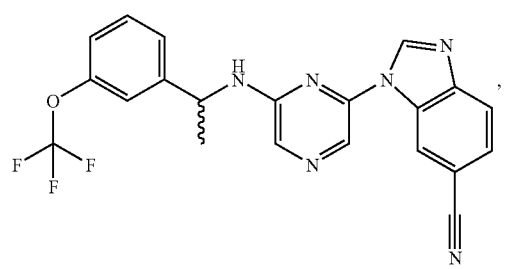
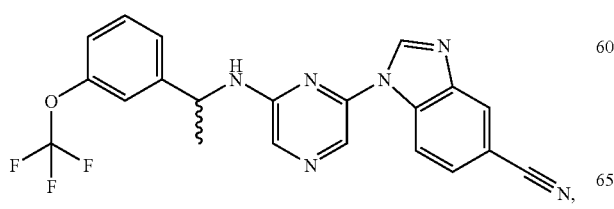
-continued
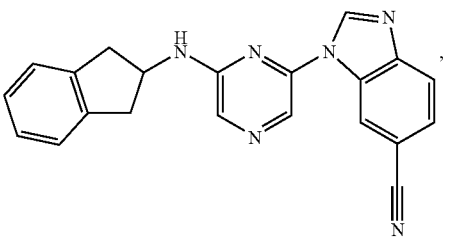
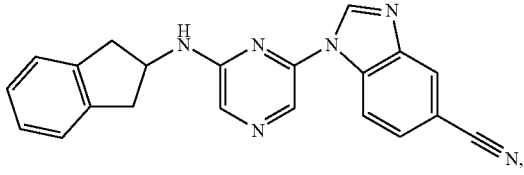
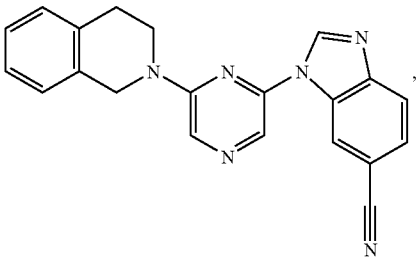
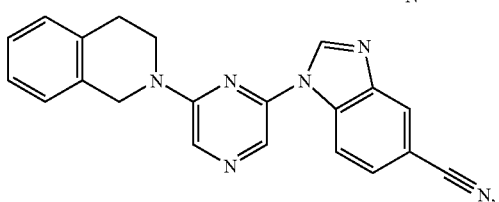
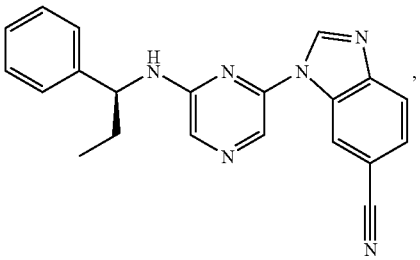
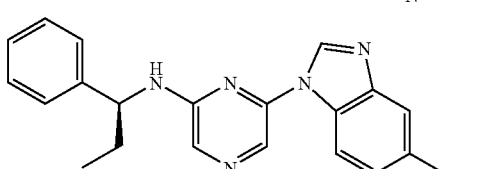
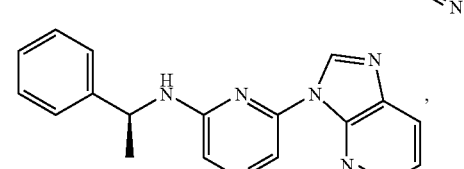
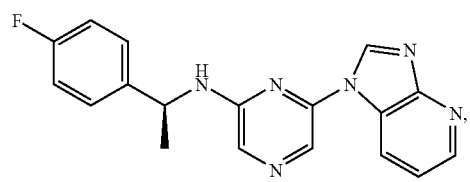

83
-continued
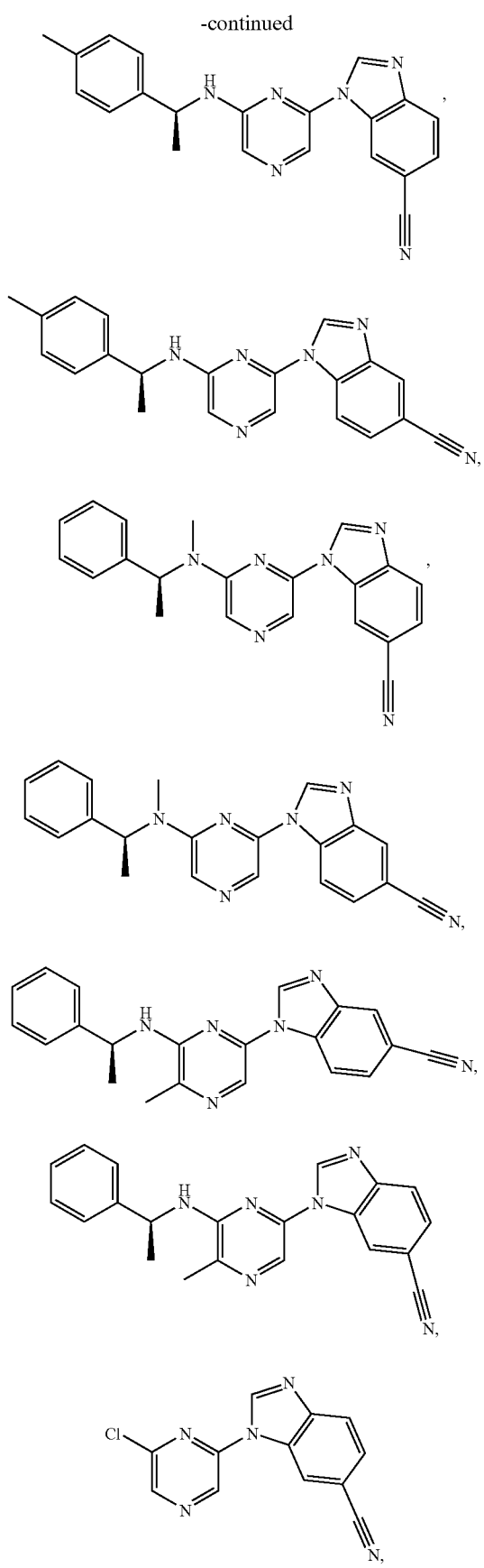
84
-continued
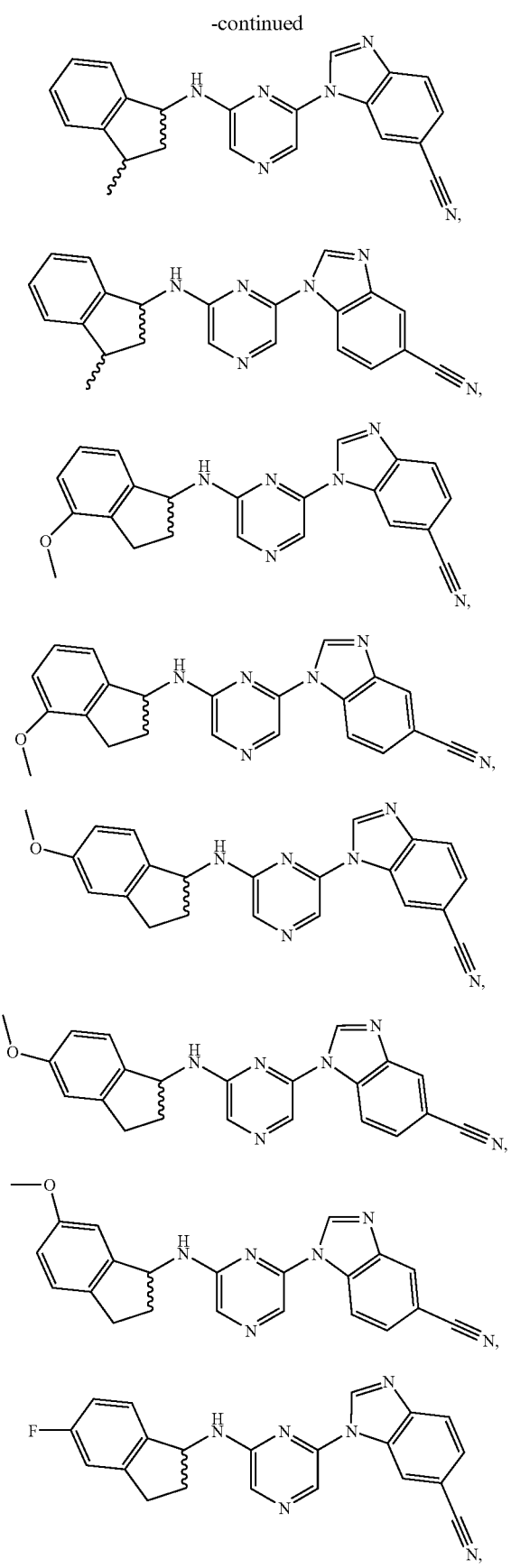

-continued

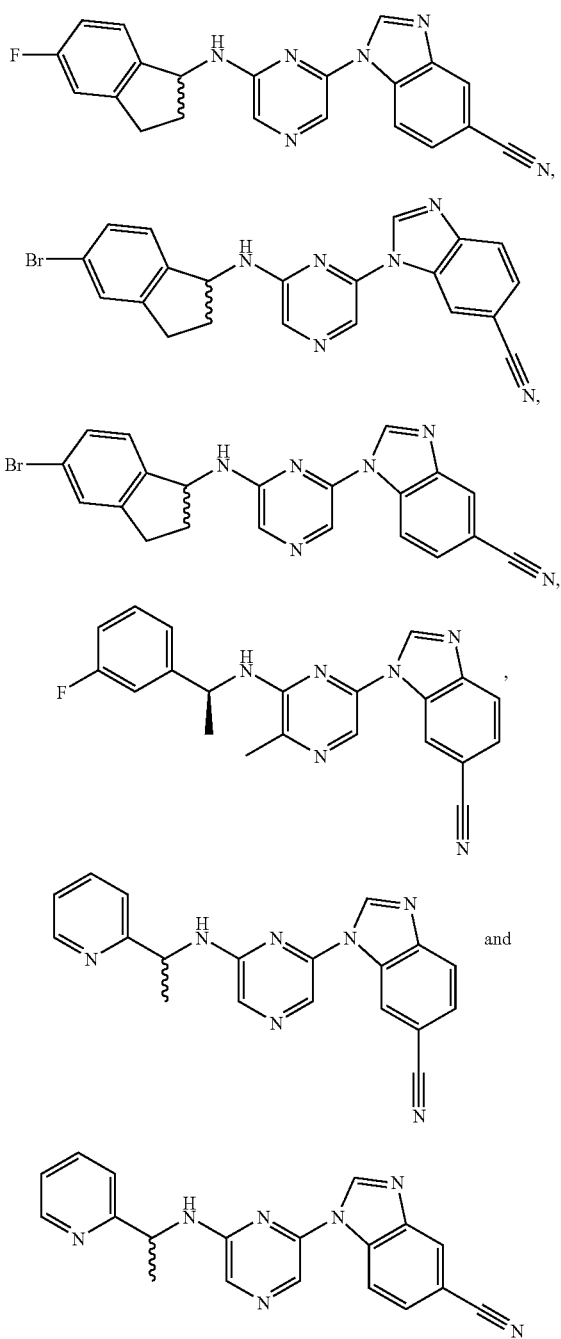

or pharmaceutically acceptable salts, or diastereomers thereof.

4. A compound selected from the group consisting of
6-(1H-Benzimidazol-1-yl)-N-benzylpyrazin-2-amine,
6-(1H-Benzimidazol-1-yl)-N-[(1R)-1-phenylethyl]pyrazin-2-amine,
6-(1H-Benzimidazol-1-yl)-N-[(1S)-1-phenylethyl]pyrazin-2-amine,
1-(6-{[1-(3-Fluorophenyl)ethyl]amino}pyrazin-2-yl)-1H-benzimidazole-5-carboxamide,
1-(6-{[1-(3-Fluorophenyl)ethyl]amino}pyrazin-2-yl)-1H-benzimidazole-6-carboxamide,
1-(6-{[1-(3-Fluorophenyl)ethyl]amino}pyrazin-2-yl)-1H-benzimidazole-6-carbonitrile,
1-[6-(3,4-Dihydroisoquinolin-2(1H)-yl)pyrazin-2-yl]-1H-benzimidazole-5-carbonitrile,
1-[6-(3,4-Dihydroisoquinolin-2(1H)-yl)pyrazin-2-yl]-1H-benzimidazole-6-carbonitrile,
1-{6-[(1S)-1,2,3,4-Tetrahydronaphthalen-1-ylamino]pyrazin-2-yl}-1H-benzimidazole-5-carbonitrile,
1-{6-[(1S)-1,2,3,4-Tetrahydronaphthalen-1-ylamino]pyrazin-2-yl}-1H-benzimidazole-6-carbonitrile,
1-(6-{[(1S)-1-Phenylethyl]amino}pyrazin-2-yl)-1H-benzimidazol-5-amine,
1-(6-{[(1S)-1-Phenylethyl]amino}pyrazin-2-yl)-1H-benzimidazol-6-amine,
N-[1-(6-{[(1S)-1-Phenylethyl]amino}pyrazin-2-yl)-1H-benzimidazol-6-yl]-2,2-dimethylpropanamide,
N-[1-(6-{[(1S)-1-Phenylethyl]amino}pyrazin-2-yl)-1H-benzimidazol-5-yl]acetamide,
N-[1-(6-{[(1S)-1-Phenylethyl]amino}pyrazin-2-yl)-1H-benzimidazol-5-yl]methanesulfonamide,
2-(S-α-Methylbenzylamino)-6-(5-(N-methylpiperazin-4-yl-methyl)-benzimidazo-1-yl)-pyrazine,
[1-(6-{[1-(4-Fluorophenyl)ethyl]amino}pyrazin-2-yl)-1H-benzimidazol-5-yl]methanol,
[1-(6-{[1-(4-Fluorophenyl)ethyl]amino}pyrazin-2-yl)-1H-benzimidazol-6-yl]methanol, and
N-[1-(4-Fluorophenyl)ethyl]-6-{6-[(4-methylpiperazin-1-yl)methyl]-1H-benzimidazol-1-yl}pyrazin-2-amine, and
a pharmaceutically acceptable salt, or diastereomer thereof.

5. The compound of claim 1, wherein said compound is:

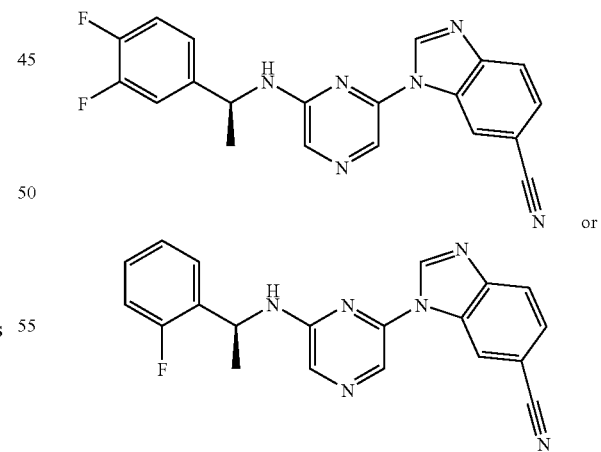

or a pharmaceutically acceptable salt, or diastereomer thereof.

6. A composition comprising a carrier and at least one compound according to claim 1.

7. The compound of claim 1, wherein Y is 1-2 substituents.

8. The compound of claim 1, wherein Y is 0 substituents and $R^2$ is $OCHF_2$, CN, $C_{1-4}$ alkylOH, $C_{1-4}$alkylhetaryl, $OC_{1-4}$ alkyl, $OC_{1-4}$alkyl$NR^3R^4$, $OC_{1-4}$alkylhetaryl, or $OC_{1-4}$ alkyl OH.

9. The compound of claim 1, wherein $R^2$ is CN.

10. The compound of claim 1, wherein $R^1$ forms a 5-8 membered ring onto the ortho position of ring A.

11. The compound of claim 10, wherein Q is CH and W is H.

12. A compound selected from a group consisting of:

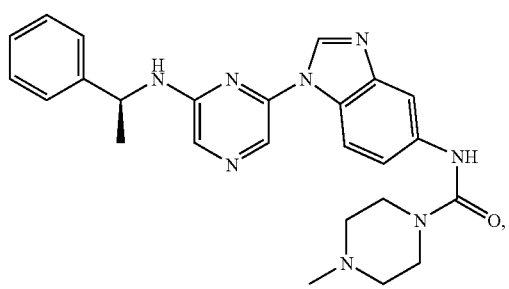

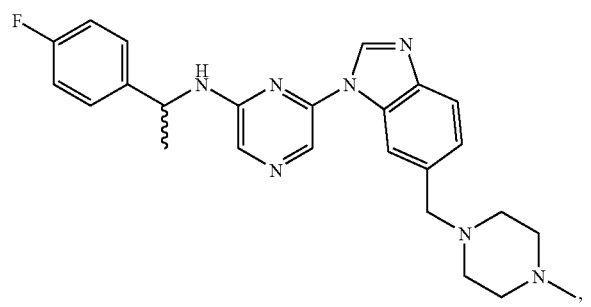

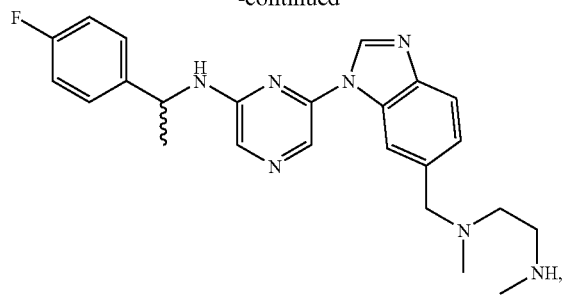

or a pharmaceutically acceptable salt, or diastereomer thereof.

* * * * *